(12) United States Patent
Fryman et al.

(10) Patent No.: US 12,340,888 B2
(45) Date of Patent: Jun. 24, 2025

(54) MEDICAL INTRAVENOUS FLUID DELIVERY AND DISPOSAL DEVICES

(71) Applicant: ICU Medical, Inc., San Clemente, CA (US)

(72) Inventors: Marshall E. Fryman, Lidenhurst, IL (US); Ujjawal Kumar, Chennai (IN); Anandaraman Vithyananthan, Chennai (IN); Pritish Jain, Chennai (IN); Syedjavid Syed Khadar, Chennai (IN); Matteo D. Picinich, Temecula, CA (US); Yun Shao Tsai, San Diego, CA (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

(21) Appl. No.: 18/068,422

(22) Filed: Dec. 19, 2022

(65) Prior Publication Data

US 2023/0130432 A1    Apr. 27, 2023

Related U.S. Application Data

(63) Continuation of application No. 16/872,176, filed on May 11, 2020, now abandoned, which is a
(Continued)

(30) Foreign Application Priority Data

Apr. 17, 2019   (IN) .............................. 201911015467

(51) Int. Cl.
*G16H 20/17* (2018.01)
*G16H 10/60* (2018.01)
(Continued)

(52) U.S. Cl.
CPC .............. *G16H 20/17* (2018.01); *G16H 10/60* (2018.01); *G16H 40/20* (2018.01); *G16H 40/63* (2018.01); *H04W 4/80* (2018.02)

(58) Field of Classification Search
CPC ........ G16H 20/17; G16H 40/20; G16H 10/60; G16H 40/63; H04W 4/80
See application file for complete search history.

(56) References Cited

U.S. PATENT DOCUMENTS

| 4,756,706 | A | 7/1988 | Kerns et al. |
| 4,898,576 | A | 2/1990 | Philip |

(Continued)

FOREIGN PATENT DOCUMENTS

| CN | 106375333 | 2/2017 |
| CN | 106913931 | 7/2017 |

(Continued)

OTHER PUBLICATIONS

ALARIS® Medical Systems, "Signature Edition® GOLD—Single & Dual Channel Infusion System", San Diego, CA, USA, date unknown, but believed to be at least as early as Nov. 29, 2008, pp. 2-88 & 2-91.

(Continued)

*Primary Examiner* — Fonya M Long
*Assistant Examiner* — Anthony Balaj
(74) *Attorney, Agent, or Firm* — Knobbe, Martens, Olson & Bear, LLP

(57) ABSTRACT

A system and method for tracking and administering liquid intravenous medications in a hospital, clinic, or patient residence, including recording information onto a short range communication device affixed to a liquid container in a hospital pharmaceutical filling or compounding center, the information including drug information, patient information, and IV administration information, transferring the liquid
(Continued)

container to a patient's bedside, programming an infusion course into a bedside IV infusion pump by enabling the pump to read the encoded information on the communication device, and disposing of the liquid container and any residual drug in a smart disposal bin that reads the communication device and weighs the container. The disposal bin may confirm the chemical contents of the container.

20 Claims, 19 Drawing Sheets

Related U.S. Application Data continuation of application No. PCT/US2020/028337, filed on Apr. 15, 2020.

(51) Int. Cl.
    *G16H 40/20*     (2018.01)
    *G16H 40/63*     (2018.01)
    *H04W 4/80*     (2018.01)

(56) References Cited

U.S. PATENT DOCUMENTS

| | | | |
|---|---|---|---|
| 4,898,578 A | 2/1990 | Rubalcaba, Jr. | |
| 5,014,714 A | 5/1991 | Millay et al. | |
| 5,014,798 A | 5/1991 | Glynn | |
| 5,041,086 A | 8/1991 | Koenig et al. | |
| 5,276,610 A | 1/1994 | Maeda et al. | |
| 5,319,363 A | 6/1994 | Welch et al. | |
| 5,356,378 A | 10/1994 | Doan et al. | |
| D352,778 S | 11/1994 | Irvin et al. | |
| 5,406,954 A | 4/1995 | Tomita | |
| 5,429,602 A | 7/1995 | Hauser | |
| 5,445,621 A | 8/1995 | Poli et al. | |
| 5,485,408 A | 1/1996 | Blomquist | |
| 5,496,273 A | 3/1996 | Pastrone et al. | |
| 5,507,412 A | 4/1996 | Ebert et al. | |
| 5,522,798 A | 6/1996 | Johnson et al. | |
| 5,547,470 A | 8/1996 | Johnson et al. | |
| 5,558,638 A | 9/1996 | Evers et al. | |
| 5,562,615 A | 10/1996 | Nassif | |
| 5,609,575 A | 3/1997 | Larson et al. | |
| 5,609,576 A | 3/1997 | Voss | |
| 5,626,151 A | 5/1997 | Linden | |
| 5,649,536 A | 7/1997 | Ogura et al. | |
| 5,681,285 A | 10/1997 | Ford et al. | |
| 5,685,844 A | 11/1997 | Marttila | |
| 5,713,856 A | 2/1998 | Eggers et al. | |
| 5,718,562 A | 2/1998 | Lawless et al. | |
| 5,743,856 A | 4/1998 | Oka et al. | |
| 5,744,027 A | 4/1998 | Connell et al. | |
| 5,752,919 A | 5/1998 | Schrimpf | |
| 5,772,635 A | 6/1998 | Dastur et al. | |
| 5,781,442 A | 7/1998 | Engleson et al. | |
| 5,782,805 A | 7/1998 | Meinzer et al. | |
| 5,792,069 A | 8/1998 | Greenwald et al. | |
| 5,803,917 A | 9/1998 | Butterfield | |
| 5,814,015 A | 9/1998 | Gargano et al. | |
| 5,935,099 A | 8/1999 | Peterson et al. | |
| 5,990,838 A | 11/1999 | Burns et al. | |
| 6,120,459 A | 9/2000 | Nitzan et al. | |
| 6,158,965 A | 12/2000 | Butterfield et al. | |
| 6,213,972 B1 | 4/2001 | Butterfield | |
| 6,241,704 B1 | 6/2001 | Peterson et al. | |
| 6,280,391 B1 | 8/2001 | Olson et al. | |
| 6,322,516 B1 | 11/2001 | Masuda et al. | |
| 6,394,958 B1 | 5/2002 | Bratteli et al. | |
| 6,405,076 B1 | 6/2002 | Taylor et al. | |
| 6,409,699 B1 | 6/2002 | Ash | |
| 6,416,291 B1 | 7/2002 | Butterfield et al. | |
| 6,456,245 B1 | 9/2002 | Crawford | |
| 6,466,671 B1 | 10/2002 | Maillard et al. | |
| 6,512,944 B1 | 1/2003 | Kovtun et al. | |
| 6,519,569 B1 | 2/2003 | White et al. | |
| 6,544,228 B1 | 4/2003 | Heitmeier | |
| 6,641,541 B1 | 11/2003 | Lovett et al. | |
| 6,689,069 B2 | 2/2004 | Bratteli et al. | |
| 6,731,989 B2 | 5/2004 | Engleson et al. | |
| 6,738,052 B1 | 5/2004 | Manke et al. | |
| 6,741,212 B2 | 5/2004 | Kralovec et al. | |
| 6,785,573 B2 | 8/2004 | Kovtun et al. | |
| 6,790,198 B1 | 9/2004 | White et al. | |
| 6,801,227 B2 | 10/2004 | Bocionek et al. | |
| 6,805,671 B2 | 10/2004 | Stergiopoulos et al. | |
| 6,898,301 B2 | 5/2005 | Iwanaga | |
| 6,985,768 B2 | 1/2006 | Hemming et al. | |
| 6,985,870 B2 | 1/2006 | Martucci et al. | |
| 6,997,905 B2 | 2/2006 | Gillespie, Jr. et al. | |
| 7,061,831 B2 | 6/2006 | de la Huerga | |
| 7,072,725 B2 | 7/2006 | Bristol et al. | |
| 7,076,062 B1 | 7/2006 | Spies | |
| 7,076,508 B2 | 7/2006 | Bourbonnais et al. | |
| 7,108,184 B2 | 9/2006 | Mase et al. | |
| 7,236,936 B2 | 6/2007 | White et al. | |
| 7,253,779 B2 | 8/2007 | Greer et al. | |
| 7,256,888 B2 | 8/2007 | Staehr et al. | |
| 7,294,109 B2 | 11/2007 | Lovett et al. | |
| 7,398,183 B2 | 7/2008 | Holland et al. | |
| 7,417,729 B2 | 8/2008 | Greenwald | |
| 7,418,981 B2 | 9/2008 | Baker et al. | |
| 7,438,216 B2 | 10/2008 | Ambekar et al. | |
| 7,471,994 B2 | 12/2008 | Ford et al. | |
| 7,483,756 B2 | 1/2009 | Engleson et al. | |
| 7,645,258 B2 | 1/2010 | White et al. | |
| 7,668,731 B2 | 2/2010 | Martucci et al. | |
| 7,698,156 B2 | 4/2010 | Martucci et al. | |
| 7,726,955 B2 | 6/2010 | Ryser et al. | |
| 7,762,989 B2 | 7/2010 | Simpson | |
| 7,782,192 B2 | 8/2010 | Jeckelmann et al. | |
| 7,839,266 B2 | 11/2010 | Hoglund et al. | |
| 7,879,025 B2 | 2/2011 | Jacobson et al. | |
| 7,927,313 B2 | 4/2011 | Stewart et al. | |
| 7,933,780 B2 | 4/2011 | de la Huerga | |
| 7,938,817 B2 | 5/2011 | Gelfand et al. | |
| 7,976,508 B2 | 7/2011 | Hoag | |
| 7,978,564 B2 | 7/2011 | de la Huerga | |
| 7,991,627 B2 | 8/2011 | Hutchinson et al. | |
| 8,011,905 B2 | 9/2011 | Artsyukhovich et al. | |
| 8,075,514 B2 | 12/2011 | Butterfield et al. | |
| 8,105,282 B2 | 1/2012 | Susi et al. | |
| 8,219,413 B2 | 7/2012 | Martinez et al. | |
| 8,221,385 B2 | 7/2012 | Estes et al. | |
| 8,285,328 B2 | 10/2012 | Caffey et al. | |
| 8,317,681 B1 | 11/2012 | Gazdzinski | |
| 8,330,579 B2 | 12/2012 | Kneip et al. | |
| 8,344,847 B2 | 1/2013 | Moberg et al. | |
| 8,347,731 B2 | 1/2013 | Genosar | |
| 8,353,288 B2 | 1/2013 | Schermeier et al. | |
| 8,355,753 B2 | 1/2013 | Bochenko et al. | |
| 8,385,972 B2 | 2/2013 | Bochenko et al. | |
| 8,394,053 B2 | 3/2013 | Bochenko et al. | |
| 8,444,595 B2 | 5/2013 | Brukalo et al. | |
| 8,452,953 B2 | 5/2013 | Buck et al. | |
| 8,463,362 B2 | 6/2013 | Fago | |
| 8,486,019 B2 | 7/2013 | White et al. | |
| 8,494,875 B2 | 7/2013 | Broselow | |
| 8,500,694 B2 | 8/2013 | Susi | |
| 8,518,021 B2 | 8/2013 | Stewart et al. | |
| 8,522,832 B2 | 9/2013 | Lopez et al. | |
| 8,545,198 B2 | 10/2013 | Artsyukhovich et al. | |
| 8,567,393 B2 | 10/2013 | Hickle et al. | |
| 8,582,421 B2 | 11/2013 | Sloan | |
| 8,606,596 B1 | 12/2013 | Bochenko et al. | |
| 8,639,525 B2 | 1/2014 | Levine et al. | |
| 8,641,672 B2 | 2/2014 | Yodfat et al. | |
| 8,652,093 B2 | 2/2014 | Lee et al. | |
| 8,676,602 B2 | 3/2014 | Broselow | |
| 8,750,896 B2 | 6/2014 | Brisebois et al. | |
| 8,756,078 B2 | 6/2014 | Collins, Jr. et al. | |
| 8,761,717 B1 | 6/2014 | Buchheit | |
| 8,777,894 B2 | 7/2014 | Butterfield et al. | |

(56) References Cited

U.S. PATENT DOCUMENTS

| | | |
|---|---|---|
| 8,777,897 B2 | 7/2014 | Butterfield |
| 8,800,881 B2 | 8/2014 | Biset et al. |
| 8,888,744 B2 | 11/2014 | Yodfat et al. |
| 8,905,965 B2 | 12/2014 | Mandro et al. |
| 8,930,704 B2 | 1/2015 | Chen |
| 8,945,043 B2 | 2/2015 | Lee et al. |
| 8,945,066 B2 | 2/2015 | Bochenko et al. |
| 8,952,794 B2 | 2/2015 | Blomquist et al. |
| 8,954,030 B1 | 2/2015 | Buchheit |
| 8,998,100 B2 | 4/2015 | Halbert et al. |
| 9,022,988 B1 | 5/2015 | Shaban |
| 9,039,655 B2 | 5/2015 | Prince et al. |
| 9,049,982 B2 | 6/2015 | Brukalo et al. |
| 9,101,307 B2 | 8/2015 | Thym et al. |
| 9,132,227 B2 | 9/2015 | Bryant, Jr. et al. |
| 9,162,026 B2 | 10/2015 | Burg et al. |
| 9,173,992 B2 | 11/2015 | Bengtsson et al. |
| 9,192,712 B2 | 11/2015 | DeBelser et al. |
| 9,218,454 B2 | 12/2015 | Kiani et al. |
| 9,227,025 B2 | 1/2016 | Butterfield et al. |
| 9,289,110 B2 | 3/2016 | Woolford et al. |
| 9,335,910 B2 | 5/2016 | Farnan et al. |
| 9,373,269 B2 | 6/2016 | Bergman et al. |
| 9,378,334 B2 | 6/2016 | Lee et al. |
| 9,391,670 B2 | 7/2016 | Brukalo et al. |
| 9,421,324 B2 | 8/2016 | Sloan |
| 9,433,718 B2 | 9/2016 | Jones |
| 9,492,071 B2 | 11/2016 | Woolford et al. |
| 9,511,184 B2 | 12/2016 | Woolford et al. |
| 9,522,224 B2 | 12/2016 | Borges et al. |
| 9,539,389 B2 | 1/2017 | Trombly et al. |
| 9,561,324 B2 | 2/2017 | Estes |
| 9,603,990 B2 | 3/2017 | Woolford |
| 9,603,995 B2 | 3/2017 | Rosinko et al. |
| 9,609,521 B2 | 3/2017 | Wang et al. |
| 9,629,901 B2 | 4/2017 | Estes |
| 9,649,431 B2 | 5/2017 | Gray et al. |
| 9,649,437 B2 | 5/2017 | Eubanks et al. |
| 9,649,438 B2 | 5/2017 | Baykal |
| 9,656,031 B2 | 5/2017 | Mandro et al. |
| 9,662,436 B2 | 5/2017 | Belkin et al. |
| 9,662,438 B2 | 5/2017 | Kamen et al. |
| 9,669,161 B2 | 6/2017 | Bryant, Jr. et al. |
| 9,700,669 B2 | 7/2017 | Burke et al. |
| 9,717,845 B2 | 8/2017 | Istoc |
| 9,740,829 B2 | 8/2017 | Blomquist |
| 9,750,872 B2 | 9/2017 | de la Huerga |
| 9,750,896 B2 | 9/2017 | Kamen et al. |
| 9,779,226 B2 | 10/2017 | Wang et al. |
| 9,808,577 B2 | 11/2017 | Nagar et al. |
| 9,849,234 B2 | 12/2017 | Baykal |
| 9,849,236 B2 | 12/2017 | Hachey et al. |
| 9,861,741 B2 | 1/2018 | Yang |
| 9,861,743 B2 | 1/2018 | Susi |
| 9,883,987 B2 | 2/2018 | Lopez et al. |
| 9,886,550 B2 | 2/2018 | Lee et al. |
| 9,889,246 B2 | 2/2018 | Woolford |
| 9,901,672 B2 | 2/2018 | Despa et al. |
| 9,907,943 B2 | 3/2018 | Grant et al. |
| 9,911,313 B2 | 3/2018 | Kelly et al. |
| 9,919,104 B2 | 3/2018 | Ohzawa |
| 9,968,734 B2 | 5/2018 | Burke et al. |
| 10,029,047 B2 | 7/2018 | Gupta et al. |
| 10,074,446 B2 | 9/2018 | Lee et al. |
| 10,112,009 B2 | 10/2018 | Dudar et al. |
| 10,137,246 B2 | 11/2018 | Estes et al. |
| 10,172,996 B2 | 1/2019 | Case et al. |
| 10,188,849 B2 | 1/2019 | Fangrow |
| 10,198,676 B2 | 2/2019 | Schindler, III |
| 10,207,047 B2 | 2/2019 | Estes |
| 10,292,641 B2 | 5/2019 | Bureau et al. |
| 2001/0044731 A1 | 11/2001 | Coffman et al. |
| 2002/0013551 A1 | 1/2002 | Zaitsu et al. |
| 2002/0029776 A1 | 3/2002 | Blomquist |
| 2002/0038392 A1 | 3/2002 | de la Huerga |
| 2002/0044059 A1 | 4/2002 | Reeder et al. |
| 2002/0077852 A1 | 6/2002 | Ford et al. |
| 2002/0085952 A1 | 7/2002 | Ellingboe et al. |
| 2003/0009244 A1 | 1/2003 | Engleson |
| 2003/0060765 A1 | 3/2003 | Campbell et al. |
| 2003/0065537 A1 | 4/2003 | Evans |
| 2003/0083583 A1 | 5/2003 | Kovtun et al. |
| 2003/0084440 A1 | 5/2003 | Lownes |
| 2003/0135087 A1 | 7/2003 | Hickle et al. |
| 2003/0139701 A1 | 7/2003 | White et al. |
| 2003/0140928 A1 | 7/2003 | Bui et al. |
| 2003/0141981 A1 | 7/2003 | Bui et al. |
| 2003/0204416 A1 | 10/2003 | Acharya |
| 2004/0068224 A1 | 4/2004 | Couvillon et al. |
| 2004/0073125 A1 | 4/2004 | Lovett et al. |
| 2004/0167465 A1 | 8/2004 | Kohler |
| 2004/0167804 A1 | 8/2004 | Simpson |
| 2004/0172283 A1 | 9/2004 | Vanderveen |
| 2004/0176984 A1 | 9/2004 | White et al. |
| 2004/0193325 A1 | 9/2004 | Bonderud |
| 2004/0193328 A1 | 9/2004 | Butterfield et al. |
| 2004/0225252 A1 | 11/2004 | Gillespie et al. |
| 2005/0055242 A1 | 3/2005 | Bello et al. |
| 2005/0062603 A1 | 3/2005 | Fuerst et al. |
| 2005/0065500 A1 | 3/2005 | Couvillon et al. |
| 2005/0107923 A1 | 5/2005 | Vanderveen |
| 2005/0145010 A1 | 7/2005 | Vanderveen et al. |
| 2005/0171815 A1 | 8/2005 | Vanderveen |
| 2005/0182366 A1 | 8/2005 | Vogt et al. |
| 2005/0204134 A1 | 9/2005 | Von Arx et al. |
| 2005/0224083 A1 | 10/2005 | Crass |
| 2006/0042633 A1 | 3/2006 | Bishop et al. |
| 2006/0047538 A1 | 3/2006 | Condurso et al. |
| 2006/0136095 A1 | 6/2006 | Rob et al. |
| 2006/0229557 A1 | 10/2006 | Fathallah et al. |
| 2006/0258985 A1 | 11/2006 | Russell |
| 2006/0265246 A1 | 11/2006 | Hoag |
| 2007/0156452 A1 | 7/2007 | Batch |
| 2007/0179448 A1 | 8/2007 | Lim et al. |
| 2007/0213598 A1 | 9/2007 | Howard et al. |
| 2007/0233035 A1 | 10/2007 | Wehba et al. |
| 2007/0233521 A1* | 10/2007 | Wehba .................. G16H 20/17 |
| | | 700/216 |
| 2007/0250339 A1 | 10/2007 | Mallett et al. |
| 2007/0257788 A1 | 11/2007 | Carlson |
| 2008/0071580 A1 | 3/2008 | Marcus et al. |
| 2008/0120492 A1 | 5/2008 | Dye |
| 2008/0172030 A1 | 7/2008 | Blomquist et al. |
| 2008/0200870 A1 | 8/2008 | Palmroos et al. |
| 2008/0300572 A1 | 12/2008 | Rankers et al. |
| 2009/0069743 A1 | 3/2009 | Krishnamoorthy et al. |
| 2009/0088731 A1 | 4/2009 | Campbell et al. |
| 2009/0112333 A1 | 4/2009 | Sahai |
| 2009/0131861 A1 | 5/2009 | Braig et al. |
| 2009/0153058 A1 | 6/2009 | Feng et al. |
| 2009/0153463 A1 | 6/2009 | Arrizza et al. |
| 2009/0153595 A1 | 6/2009 | Cozmi et al. |
| 2009/0157432 A1 | 6/2009 | Palmroos et al. |
| 2009/0171289 A1 | 7/2009 | Davis et al. |
| 2009/0177180 A1 | 7/2009 | Rubalcaba et al. |
| 2009/0177991 A1 | 7/2009 | Davis et al. |
| 2009/0177992 A1 | 7/2009 | Rubalcaba et al. |
| 2009/0183105 A1 | 7/2009 | Teel et al. |
| 2009/0183147 A1 | 7/2009 | Davis et al. |
| 2009/0212966 A1 | 8/2009 | Panduro |
| 2009/0266358 A1 | 10/2009 | Rock et al. |
| 2009/0270810 A1 | 10/2009 | DeBelser |
| 2010/0022988 A1 | 1/2010 | Wochner |
| 2010/0077198 A1 | 3/2010 | Buck |
| 2010/0217621 A1 | 8/2010 | Schoenberg |
| 2010/0271218 A1 | 10/2010 | Hoag et al. |
| 2011/0067781 A1* | 3/2011 | Osborne ................ B65B 55/00 |
| | | 141/37 |
| 2011/0241878 A1* | 10/2011 | Hoag .................... A61B 90/98 |
| | | 340/10.5 |
| 2011/0257798 A1 | 10/2011 | Ali et al. |
| 2011/0259954 A1 | 10/2011 | Bartz et al. |
| 2011/0295196 A1 | 12/2011 | Chazot et al. |
| 2011/0320049 A1 | 12/2011 | Chossat et al. |

(56) References Cited

U.S. PATENT DOCUMENTS

| | | |
|---|---|---|
| 2012/0041778 A1 | 2/2012 | Kraft |
| 2013/0006666 A1 | 1/2013 | Schneider |
| 2013/0091556 A1 | 4/2013 | Horn et al. |
| 2013/0253946 A1 | 9/2013 | Broselow |
| 2013/0274669 A1* | 10/2013 | Stempfle ............. A61M 5/1456 604/151 |
| 2013/0291116 A1 | 10/2013 | Homer |
| 2014/0054883 A1 | 2/2014 | Lanigan et al. |
| 2014/0074493 A1 | 3/2014 | Schneider et al. |
| 2014/0107579 A1 | 4/2014 | Lanigan et al. |
| 2014/0111801 A1 | 4/2014 | Cohen |
| 2014/0136229 A1 | 5/2014 | Levine et al. |
| 2014/0188516 A1* | 7/2014 | Kamen ................ G16H 20/17 705/3 |
| 2014/0257251 A1 | 9/2014 | Bush et al. |
| 2014/0259837 A1 | 9/2014 | Belliveau et al. |
| 2014/0265611 A1 | 9/2014 | Fern et al. |
| 2014/0276564 A1 | 9/2014 | Schneider |
| 2014/0358082 A1 | 12/2014 | Ohzawa |
| 2014/0364828 A1 | 12/2014 | Nusbacher et al. |
| 2014/0378903 A1 | 12/2014 | Quinlan |
| 2015/0011970 A1 | 1/2015 | Kamen et al. |
| 2015/0094660 A1 | 4/2015 | Mandro et al. |
| 2015/0112264 A1 | 4/2015 | Kamen et al. |
| 2015/0161339 A1 | 6/2015 | Teucher et al. |
| 2015/0165118 A1 | 6/2015 | Lee et al. |
| 2015/0174320 A1 | 6/2015 | Grant et al. |
| 2015/0182697 A1 | 7/2015 | Panzer |
| 2015/0182698 A1 | 7/2015 | Panzer |
| 2015/0223732 A1 | 8/2015 | Prince et al. |
| 2015/0230760 A1 | 8/2015 | Schneider |
| 2015/0300725 A1 | 10/2015 | Halbert |
| 2015/0304478 A1 | 10/2015 | Kim et al. |
| 2015/0314063 A1 | 11/2015 | Nagar et al. |
| 2015/0328396 A1 | 11/2015 | Adams et al. |
| 2015/0367065 A1 | 12/2015 | Adams et al. |
| 2016/0001003 A1* | 1/2016 | Perazzo ............. A61M 5/1782 53/493 |
| 2016/0015887 A1 | 1/2016 | Pananen et al. |
| 2016/0015911 A1 | 1/2016 | Bazargan et al. |
| 2016/0036590 A1 | 2/2016 | Barthe |
| 2016/0038675 A1 | 2/2016 | Estes et al. |
| 2016/0051750 A1* | 2/2016 | Tsoukalis ............ A61M 5/1689 235/375 |
| 2016/0055317 A1 | 2/2016 | Levine et al. |
| 2016/0074573 A1 | 3/2016 | Kohlbrecher |
| 2016/0158108 A1* | 6/2016 | Gofer ........................ A61J 1/03 206/539 |
| 2016/0158437 A1 | 6/2016 | Biasi et al. |
| 2016/0199572 A1 | 7/2016 | Yang |
| 2016/0213851 A1* | 7/2016 | Weibel ............... A61B 5/14532 |
| 2016/0228633 A1 | 8/2016 | Welsch et al. |
| 2016/0287780 A1 | 10/2016 | Lee et al. |
| 2016/0334348 A1 | 11/2016 | Jones |
| 2016/0339168 A1 | 11/2016 | Hutchinson et al. |
| 2016/0345830 A1 | 12/2016 | Raisoni et al. |
| 2016/0345874 A1 | 12/2016 | Raisoni et al. |
| 2016/0346469 A1 | 12/2016 | Shubinsky et al. |
| 2017/0007750 A1 | 1/2017 | Woolford et al. |
| 2017/0020191 A1 | 1/2017 | Lamb et al. |
| 2017/0021093 A1 | 1/2017 | Elder et al. |
| 2017/0065763 A1 | 3/2017 | Rossitto et al. |
| 2017/0086248 A1 | 3/2017 | Sloan |
| 2017/0098058 A1 | 4/2017 | McCullough et al. |
| 2017/0100536 A1 | 4/2017 | Estes |
| 2017/0129763 A1 | 5/2017 | Fangrow, Jr. |
| 2017/0132867 A1 | 5/2017 | Berg et al. |
| 2017/0136177 A1 | 5/2017 | Lee et al. |
| 2017/0142658 A1 | 5/2017 | Kruse |
| 2017/0165412 A1 | 6/2017 | Kelly et al. |
| 2017/0185747 A1 | 6/2017 | Yu et al. |
| 2017/0206336 A1 | 7/2017 | Lee et al. |
| 2017/0209644 A1 | 7/2017 | Browka et al. |
| 2017/0213012 A1 | 7/2017 | O'Scolai et al. |
| 2017/0216519 A1 | 8/2017 | Vouillamoz et al. |
| 2017/0224429 A1 | 8/2017 | Fung et al. |
| 2017/0224935 A1 | 8/2017 | Hoffmann et al. |
| 2017/0235919 A1 | 8/2017 | Bauss et al. |
| 2017/0246380 A1 | 8/2017 | Rosinko et al. |
| 2017/0252522 A1 | 9/2017 | Mandro et al. |
| 2017/0266381 A1 | 9/2017 | Bryant, Jr. et al. |
| 2017/0281866 A1 | 10/2017 | Nakanishi |
| 2017/0304541 A1 | 10/2017 | Bauss et al. |
| 2017/0316177 A1 | 11/2017 | Mirov et al. |
| 2017/0319780 A1 | 11/2017 | Belkin et al. |
| 2017/0319787 A1 | 11/2017 | Roedle |
| 2017/0360366 A1 | 12/2017 | Potes et al. |
| 2018/0008770 A1 | 1/2018 | Savoie et al. |
| 2018/0008788 A1 | 1/2018 | Kamen et al. |
| 2018/0060529 A1 | 3/2018 | Crothall et al. |
| 2018/0081669 A1 | 3/2018 | Becker et al. |
| 2018/0096121 A1 | 4/2018 | Goeringer et al. |
| 2018/0147345 A1 | 5/2018 | Petäinen et al. |
| 2018/0197624 A1 | 7/2018 | Robaina et al. |
| 2018/0300994 A1 | 10/2018 | Nelson et al. |
| 2019/0010435 A1 | 1/2019 | Norderhaugh et al. |
| 2019/0046035 A1 | 2/2019 | Nyquist |
| 2022/0254470 A1* | 8/2022 | Lafauci ............. G06Q 10/0631 |

FOREIGN PATENT DOCUMENTS

| | | |
|---|---|---|
| CN | 108337670 | 7/2018 |
| EP | 1 197 178 | 4/2002 |
| EP | 3 422 225 | 1/2019 |
| IN | 00897/che/2014 | 2/2014 |
| JP | 2009-148592 | 7/2009 |
| JP | 5716879 | 3/2015 |
| WO | WO 03/094092 | 11/2003 |
| WO | WO 2004/070994 | 8/2004 |
| WO | WO 2013/095459 | 6/2013 |
| WO | WO 2014/085395 | 6/2014 |
| WO | WO 2017/144366 | 8/2017 |
| WO | WO 2018/013842 | 1/2018 |
| WO | WO 2018/022355 | 2/2018 |
| WO | WO 2018/217605 | 11/2018 |
| WO | WO 2020/214717 | 10/2020 |

OTHER PUBLICATIONS

Comodo, "EV Code Signing Certificate" https://web.archive.org/web/20170610185454/https://ssl.comodo.com/code-signing/extended-validation/, archived Jun. 10, 2017 in 2 pages.

Coppola et al., "BD Introduces Simplified Comprehensive IV Management", Dec. 7, 2015, https://www.bd.com/en-us/company/new-and-media/press-releases/dec-7-2015-bd-introduces-simplified-comprehensive-iv-management in 3 pages.

International Search Report and Written Opinion received in PCT Application No. PCT/US2020/028337, dated Jul. 9, 2020 in 18 pages.

Smith et al., "Security in Health-Care Information Systems—Current Trends", International Journal of Medical Informatics, 1999, vol. 54, pp. 39-54.

Vakulenko, Michael, "Mbed Cloud Makes Device Passwords a Thing of the Past", https://blog.pellon.com/post/mbed-cloud-secure-devices, Mar. 2018 in 3 pages.

* cited by examiner

MEDICAL INTRAVENOUS FLUID DELIVERY AND DISPOSAL DEVICES

CROSS-REFERENCE TO RELATED APPLICATIONS

This is a continuation of U.S. patent application Ser. No. 16/872,176, filed on May 11, 2020, which claims the benefit under 35 U.S.C. § 120 and 35 U.S.C. § 365(c) as a continuation of International Application No. PCT/US2020/028337, designating the United States, with an international filing date of Apr. 15, 2020, which claims priority to Indian Provisional Patent Application No. 201911015467, filed Apr. 17, 2019, the entire contents of each of which are incorporated by reference herein and made a part of this specification.

BACKGROUND OF THE INVENTION

Field

This development relates generally to medical devices and specifically to intravenous fluid delivery and disposal devices.

Description of the Related Art

Many types of medical fluids are routinely used to treat patients, including chemotherapy drugs, antibiotics, immunosuppressive drugs, antiviral drugs, hydrating fluids, nourishing fluids, anticoagulants, pain management drugs, contrast fluids for medical imaging, etc. All of these fluids, in turn, come in many different varieties with advantages and disadvantages for various types of diseases, conditions, injuries, or therapies. Moreover, particular patients require optimized dosages, concentrations, and combinations of these drugs or other medical fluids to address their specific medical needs. As a result, medical facilities are required to provide many different types of customized medical fluids on a continual basis to meet individual patient needs.

Modern medical care often involves the use of medical pump devices to deliver fluids and/or fluid medicine to patients. Medical pumps permit the controlled delivery of fluids to a patient, and such pumps have largely replaced gravity flow systems, primarily due to the pump's much greater accuracy in delivery rates and dosages, and due to the possibility for flexible yet controlled delivery schedules. However, modern medical devices, including medical pumps, can be complicated and time-consuming for caregivers to program. Medical facilities struggle to provide appropriate caregiver staffing levels and training while holding down the cost of medical care. Human errors in pump programming and other medication errors can have serious consequences for the patient. Medication errors, which are sometimes referred to as adverse drug events (ADE), can increase the length of hospital stay and the cost of medical care for the patients involved or their healthcare insurance carrier.

Moreover, many types of medical fluids are tightly regulated by governmental authorities because they can be harmful or addictive to those not under the care of a medical professional. This can lead to possible abuse of medical fluids by various parties, including the improper use of residual medical fluid remaining after partial use by a prescribed patient. A similar situation can exist for medicinal patches, carpules, vials, and syringes.

SUMMARY

In some embodiments, a medical fluid container can include an electronically writable and readable label on which information relating to the medical fluid, the intended patient, and/or the intended administration of the drug to the patient can be encoded and stored for later use. The medical fluid container can be configured to receive a customized medical fluid for a particular patient comprising one or more fluid components. In some embodiments, this fluid can be identified in terms of a specific spectrographic profile, a specific weight or specific gravity or other analog to weight, and/or with one or more other characteristics. In some embodiments, the medical fluid comprises one or more drugs. The one or more drugs may initially be provided in a bulk or concentrated or separate form, and may therefore need to be compounded, transported, stored, and dispensed at specific temperatures to a patient. Further, it may be advantageous for certain medical fluids to be closely monitored or controlled such that an unauthorized attempt to penetrate or otherwise access the contents of the container of the medical fluid can be detected to prevent adulteration or modification by either unauthorized adding or removing of fluid.

The medical fluid container can be transported from a pharmacy or filling or compounding station to a patient area and removably attached to an electronic intravenous infusion pump near the patient, where the pump can electronically read one or more portions of the information encoded onto the label of the container and can automatically program the pump, either partially or completely, to perform the administration or course of treatment with the medical fluid for the patient, without requiring a health care professional or patient to separately enter all or any of such information directly into the pump. The pump may also verify one or more characteristics of the medical container or medical fluid in the container, such as the weight, specific gravity, or other weight analog, or any other characteristic of the medical container or medical fluid, to verify that the medical container or medical fluid is the same or has substantially the same characteristics as when it was filled, compounded, or otherwise prepared. If there is a clinically significant or material deviation outside of normal parameters in the one or more characteristics of the medical container or medical fluid, the pump can alert the user, the attending healthcare professional, or an information system.

The medical container may also include one or more items of compliance data or compliance measuring devices, such as a time stamp, a timer, and/or one or more environmental sensors, such as a temperature sensor. The label may have encoded thereon acceptable ranges of time periods and environmental conditions in which the medical container can be transported, stored, and/or used. The pump can verify that the medical container or medical fluid has been properly transported and stored within the acceptable ranges of time and one or more environmental conditions. The pump can perform a thermic change operation (e.g., heating or cooling of the medical container or medical fluid) to bring the current temperature of the fluid to the correct dispensing temperature and then monitor the temperature during administration of the fluid to ensure it remains compliant and to make appropriate thermic adjustments. The pump may use encoded information and/or one or more timers and/or environmental sensors to verify that the container has not become adulterated.

In performing a customized course of infusion for a particular patient, the infusion system is not required to communicate with or store information in a medical record system or electronic health record, but can instead communicate or store all necessary information for the course of infusion through the label affixed to the medical fluid container. This includes the ability to write changes to the label so that, in the event of further transport, the label can act as the source of information for the medical fluid rather than an external source. Before, during, and after use of the medical fluid, the medical fluid container and those persons who administer, use, and transport it can be tracked and the contents of the medical fluid container can be verified beginning with the initial filling or compounding stage to the ultimate disposal stage. In some embodiments, the system can save time and resources, and lower the risk of human errors and abuses.

DETAILED DESCRIPTION OF PREFERRED EMBODIMENTS

Figure 1A:
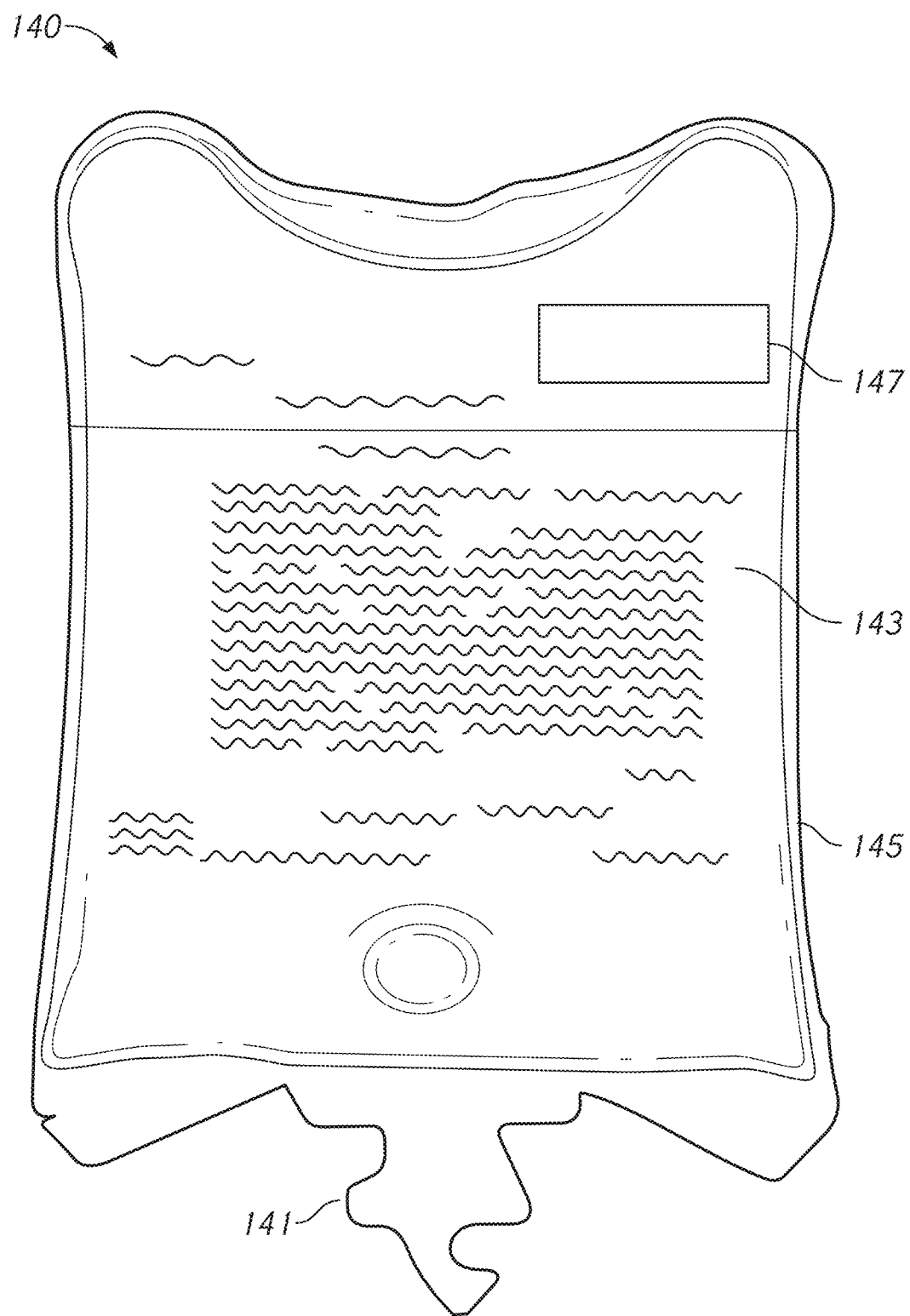
FIG. 1A is an illustration of an example of a medical fluid container comprising an electronically writable and readable label.

Various systems, methods, and components can be used in different embodiments of the inventions. Some embodiments are illustrated in the accompanying figures; however, the figures are provided for convenience of illustration only, and should not be interpreted to limit the inventions to the particular combinations of features shown. Rather, any feature, structure, material, step, or component of any embodiment described and/or illustrated in this specification can be used by itself, or with or instead of any other feature, structure, material, step, or component of any other embodiment described and/or illustrated in this specification. Nothing in this specification is essential or indispensable.

In the figures and the description that follows, like reference numerals generally refer to like components or steps. Definitions are provided below for some terms that appear in this description. "Medical device" includes without limitation a filling or compounding apparatus, a pump, medical containers, connectors, and tubing, a monitor for monitoring patient vital signs or other parameters, an electronic diagnostic device, etc. Typically, a medical device is located in a particular physical location or clinical care area (CCA) within a hospital or some other environment. In some embodiments, the medical device has a logical identifier or logical address and, when in contact with a communication network, has a network internet protocol or IP address if it is on a communication network. "Pump" includes without limitation a device that acts upon a cassette, reservoir, vial, syringe, tubing, or other fluid container to convey medication or fluid to or from a patient (for example, without limitation, an enteral pump, an infusion pump, a patient controlled analgesia (PCA) or pain management medication pump, or a suction pump. "Medication" as used herein is something that has a physiological impact on a person or animal, including but not limited to liquid or gaseous fluids, drugs or medicines, liquid nutritional products and combinations thereof. Medications that are delivered or prepared for delivery intravenously to patients are generally in liquid form, and are thus also referred to herein as "solutions."

"Label" as used herein includes without limitation an electronic tag or device (including a tag or device without a processor) that is capable of providing information in electronic form about: (a) a medical fluid container (e.g., an order or prescription from the physician or other healthcare provider the medical fluid, the type of fluid, the expiration date of the fluid, the concentration of the fluid, the weight of the fluid, the appearance of the fluid, the constituents or components of the fluid, handling or disposal instructions for the fluid, etc.); (b) the patient to whom the medical fluid is intended to be administered (e.g., the name, sex, weight, age, medical condition, location, allergy condition, medical history, etc. of the patient); (c) the administration of the medical fluid to the patient (e.g., the time duration of administration, the frequency of administration, the drip rate or flow rate of administration, etc.); and/or (d) any other information necessary or useful for a course of infusion, including specific gravity or weight analog, fluid temperature(s) required over its lifecycle, and information about container integrity such that it resists adulteration. A label can include without limitation a near-field communication device or a radio-frequency identification device. In some embodiments, an onboard label can be permanently or temporarily affixed to a medical fluid container in a manner that resists removal or tampering without tools and/or without destroying or damaging the label.

FIG. 1A illustrates an example of a medical fluid container 140 such as an intravenous (IV) fluid storage bag, which can comprise a fluid 143 such as a therapeutic liquid or medicated liquid or drug, a partially or entirely translucent, flexible, substantially impermeable polymer wall 145 configured to enclose the fluid 143, and one or more fluid access regions 141 such as one or more connectors, pierceable septa, and/or resealable valves. The medical fluid container 140 can include an electronically writable and readable information-storage and retrieval device 147, such as an electronic label in the form of a near-field communication device or radio-frequency identification (RFID) device. All descriptions in this specification of medical fluid containers or drug containers or the like should be viewed as being applicable also to any other medical administering devices, including medicinal patches, carpules, vials, and syringes.

Figure 1B:
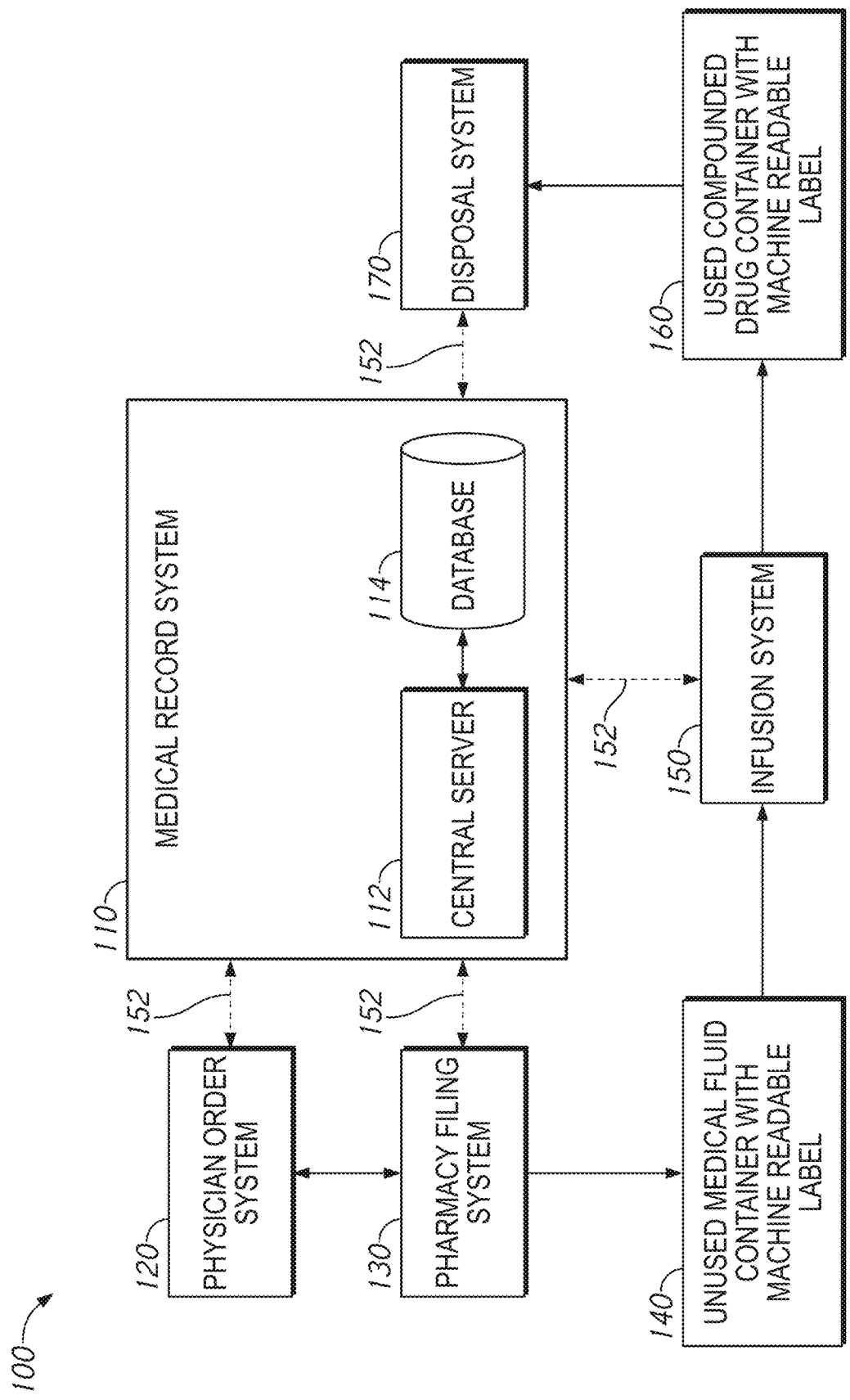
FIG. 1B is a diagram illustrating an example system for encoding of intravenous administration and secure disposal.

FIG. 1B illustrates an example system 100 for encoding of intravenous administration and secure disposal of patient medication. Hospital information systems typically include one or more computers hard-wired together into a network 152 by cabling, interfaces, and/or Ethernet connections. Alternatively, wireless connections and communications can be used in whole or in part utilizing a wireless communications protocol, such as IEEE 801.11, IEEE 802.11, Bluetooth, WiFi, Zigbee, or any other suitable wireless technologies. A medical record system 110 may include a central server 112 in communication with a database 114. Servers provide processing capability and memory for storage of data and various application programs, modules or systems, including but not limited to a computerized physician order entry system 120 in communication with the medical record system 110 via the network 152. A pharmacy filling or compounding system or fluid transfer system 130 is also in communication with the medical record system 110 via the network 152. Hospital personnel, such as physicians, pharmacists, technicians and other clinical personnel can be authorized to access these modules or systems through client workstations connected to the servers in order to enter data, access information, run reports and complete other tasks.

An end product of the pharmacy filling or compounding system 130 may include an unused drug container 140 with an affixed machine writable and readable label. The unused drug container 140 is transported to a medicine storage area or a nurse station in a hospital, or is transported to patient's residence for use in an infusion system 150. The infusion system 150 can be in communication with the medical record system 110 via the network 152. After the drug or medicine is administered via infusion into a patient by the infusion system 150, a used drug container 160 with the affixed machine writable and readable label with any remaining drug or medicine is then transported to a disposal system 170 for secure disposal of the used container 160 along with any remaining drug or medicine.

Certain activities related to patient care typically take place in a hospital environment. Upon admission to a hospital, in certain embodiments, an admission clerk or similar personnel enters demographic information about each patient into the database 114. Each patient is issued a patient identification wristband, bracelet or tag that includes an identifier, such as a barcode or RFID tag for example, representing a unique set of characters, typically a patient ID or medical record number, identifying the patient, sometimes referred to as patient specific identification information. The wristband, bracelet or tag may also include other information, in machine readable or human-readable form, such as the name of the patient's doctor, blood type, allergies, etc. as part of the patient specific identification information.

The patient's doctor prescribes medical treatment by entering an order into the physician order system 120. The order, as prescribed, may specify any useful or necessary information, such as a start time, stop time, a range of allowable doses, drug concentration, infusion rate (volume over time), physiological targets, route, and/or site of administration, etc. In the case of an order for infusion of fluids or medication, the order may be written in various formats, but typically includes the patient's name, patient ID number, a unique medication order or prescription number, a medication name, medication concentration, a dose or dosage, frequency, and a time of desired delivery. This information is entered into the database 114 in certain embodiments.

The medication order is also delivered electronically to the pharmacy filling or compounding system 130 in the pharmacy and is stored in an associated memory. The pharmacist screens the prescribed order, translates it into an order for dispensing medication, and prepares or directs a technician to prepare the medication or fluids with the proper additives and/or necessary diluents. The prescribed order may include information such as the specific gravity or other weight analog of the final compounded fluid, the temperature information for the lifecycle of the fluid, and whether or not adulteration detection is required. As described in conjunction with FIG. 2, the pharmacist or technician prepares and/or affixes a label or the pharmacist or technician inputs directly or indirectly information on a previously prepared and/or affixed label. In some embodiments, the pharmacy filling system 130 includes an onboard label-writing component that is configured to automatically transfer or record one or more items of information that are needed or useful in performing a patient infusion, including some or all of the information provided in the foregoing description of a "label." Any information described anywhere in this specification can be included in the label. In some embodiments, a secondary label or an overwrap label that covers some or all of the container may be provided to allow for more control of fluid container properties such as, but not limited to, temperature and adulteration, modification, or tampering detection.

In some embodiments, the pharmacy filling system 130, or another electronic component that is disconnected or disassociated with the pharmacy filling system 130, can include a data-entry keypad or other user-input device that enables a user to manually input information that the pharmacy filling system 130 or other electronic component can then write or record electronically onto the onboard label. In some embodiments, information from the medical record system 110 can be transferred or written onto the onboard label. The information on the onboard label can include drug container specific information to a medication or drug container 264. In certain embodiments, the label can include in machine readable form an order ID and a patient ID, which is usually a medical record number along with medical device specific delivery information including but not limited to the dispense ID number, patient ID, drug name, drug concentration, container volume, VTBI, rate or duration, temperature of the medication during its lifecycle, adulteration detection information, specific gravity or other weight analog that indicates the final compounded fluid weight, etc. In some embodiments, a partial collection of the variables (e.g., two of three variables, such as VTBI, rate and duration) are provided, as one or more others can be calculated when some are known. The labeled medication typically is delivered to a secure, designated staging location or mobile drug cart on the ward or floor near the patient's room or treatment area. Any information useful for a patient's course of treatment can be included in the label.

The medication order pending dispensing or administration can be posted to a task list in the medical record system 110 or can be saved in the medical record system 110 or can be used to update or provide history in the medical record system 110; however, in some embodiments all information needed to properly identify a patient and perform an administration of medical fluid on the patient can be stored and retrieved electronically directly to or from the onboard label of the medical fluid container, without requiring communication with the centralized electronic medical record system. For example, in some embodiments, there is no communication required and/or performed between the physician order system 120 and the medical record system 110, between the pharmacy filling system 130 and the medical record system 110, between the infusion system 150 and the medical record system 110, and/or between the disposal system 170 and the medical record system 110. The infusion system can provide sufficient infusion information to perform patient infusions in healthcare locations where there is no centralized electronic medical record system or where it is desirable not to use the medical record system 110 or its associated communication media or networks for some or all of the information relating to an infusion course.

In some embodiments, this infusion system is more robust and resilient against certain long and short term electronic failures because its customized performance for a particular patient does not depend upon communication over a network with a centralized medical record system. In some embodiments, by not requiring communication with the centralized medical record system, the infusion system can: (a) diminish security risks and obviate compliance with regulations relating to communication of patient information over networks or wireless protocols; (b) increase the electronic network bandwidth available for other applications in a healthcare facility; and/or (c) provide a more reliable, resilient patient infusion system that is not vulnerable to network malfunctions and/or power outages. Not all embodiments of the infusion system will achieve all or any of these objectives.

Figure 2:
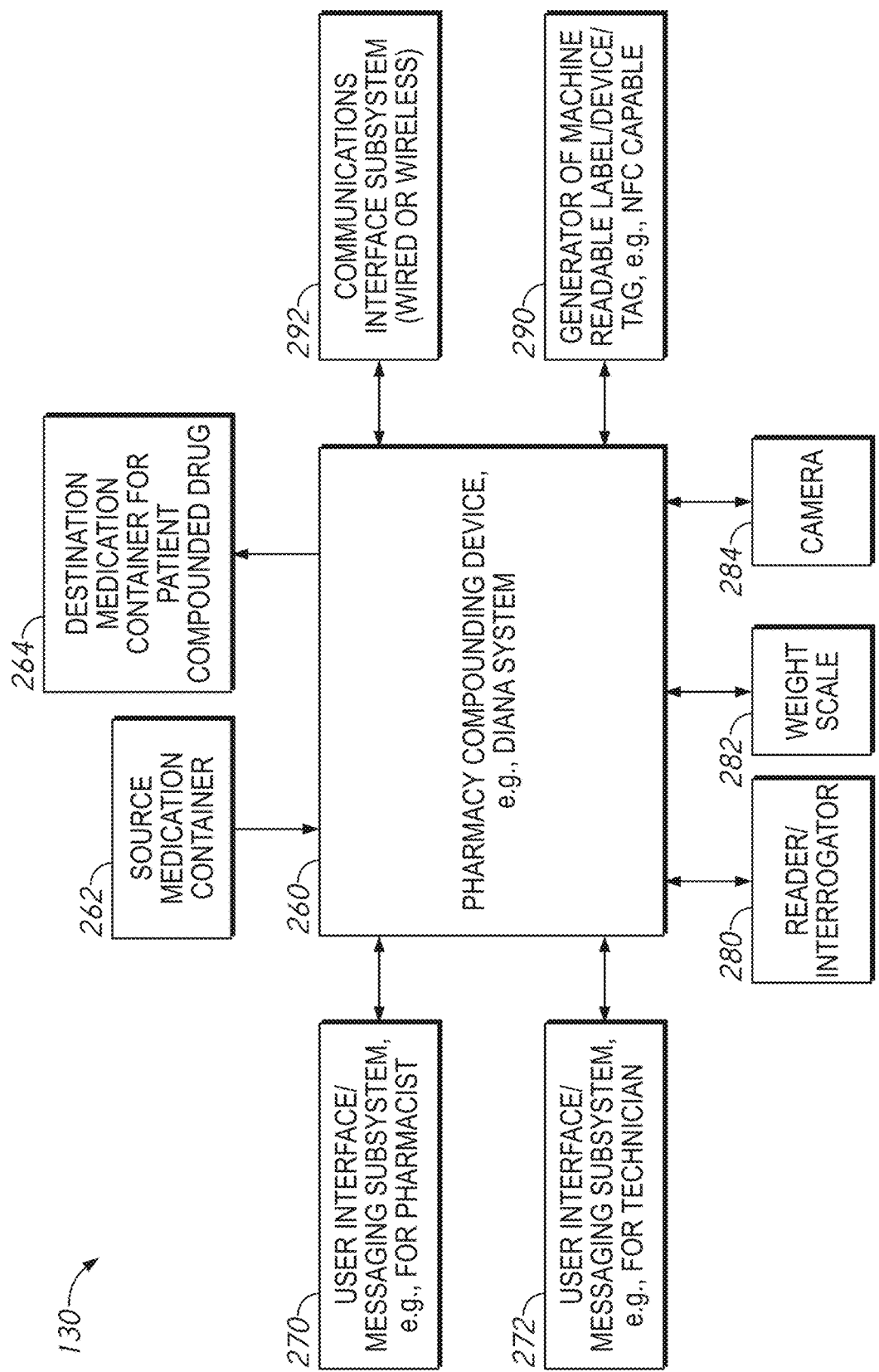
FIG. 2 is a diagram illustrating an example automated pharmacy filling or compounding system such as shown in FIG. 1B.

FIG. 2 is a schematic illustration of an example fluid transfer or pharmacy filling or compounding device 260 removably attached to and/or in selective communication with other components of a fluid transfer or pharmacy filling or compounding system 130 shown in FIG. 1. In certain embodiments, the fluid transfer device may be a Diana™ device available from ICU Medical, Inc. In some embodiments, the filling or compounding system 130 may include a source medication container 262, the fluid transfer or filling or compounding device 260 including an electromechanical controller (not shown), and a destination medication container 264. The source container 262 and the fluid destination container 264 can each comprise any suitable device for holding or supplying medical fluids, such as a vial, a bottle, a bag, a hose, a tube, a tank, a canister, etc. In some embodiments, the fluid destination container 264 is a type of container that is selected to be particularly well suited in size and structure for easy and convenient storage or transportation from a fluid transfer station to a patient treatment location, such as an intravenous fluid storage bag or IV bag, to provide an individual-patient, single-dosage supply of medical fluid. In some embodiments, the source container 262 is a type of container that is sufficiently large to provide multiple single-patient doses to be transferred into multiple destination containers 264 (either serially or in parallel). Some examples of fluid transfer devices 260 are illustrated and described in U.S. Pat. Nos. 8,522,832; 9,883, 987; PCT Publication No. WO 2016/010909; and U.S. Pat. No. 9,849,236, all of which are incorporated by reference in their entireties and made a part of this specification, and any feature, structure, material, step, or component of any embodiment described and/or illustrated in any of these can be used with or instead of any other feature, structure, material, step, or component of any embodiment described and/or illustrated elsewhere in this specification.

The fluid transfer or pharmacy filling or compounding system 130 includes a user interface/messaging subsystem 270, such as for use by a pharmacist, that is in communication with the fluid transfer or pharmacy filling or compounding device 260. The fluid transfer or pharmacy filling or compounding system 130 may also include a user interface/messaging subsystem 272, such as for use by a technician, that is also in communication with the fluid transfer or pharmacy filling or compounding device 260. The pharmacist may screen the prescribed order, translate it into an order for dispensing medication, and prepare or direct a technician to prepare the medication or fluids with the proper additives and/or necessary diluents. The fluid transfer or pharmacy filling or compounding system 130 includes a communications interface subsystem 292, which can be a wired or wireless way for the filling or compounding device to communicate with the hospital information systems, such as the medical record system 110. This communication path can be used to record the details of the medicine and/or the information about the patient and administration instructions for the medication in the database 114, for example.

A reader/interrogator 280 connected to the filling or compounding device 260 may be used by the pharmacist and/or technician such as to scan in a coded label of the medication, fluid, additives and/or diluents. A weight scale 282 and an optional camera 284 are also in communication with the filling or compounding device 260. The weight scale can be used to weigh the drug or medicine and the camera can be used to record images at any stage of the filling or compounding process. Examples of cameras or readers that may be used are the Arducam Noir Camera for Rasberry Pi, the Waveshare RPi camera, or the RFIDeas pcProx Plus reader.

The fluid transfer or pharmacy filling or compounding system 130 also includes a generator 290 of an encoded machine readable label to be affixed on the medication container of the medicine. Examples of label generators or printers include UHF label printers such as the Zebra ZD500R or NFC label printers such as the Sato CL4NX HF. In certain embodiments, the information printed or stored on the electronic or machine readable label includes information about the patient, the medication, and administration instructions, such as for programming the infusion system 150. In certain embodiments, the camera 284 captures an image of the label affixed on the medication container of the medicine.

In some embodiments, an infusion pump or another electronic station that is accessible by the patient (e.g., at the patient's bedside, in a patient's home, on a table near the patient, near an infusion chair, etc.) or at a nursing station or elsewhere can be equipped with an independent reader and/or writer for electronic labels that can be utilized to update or modify the contents of the label. For example, in some situations, a medical fluid container can be provided to the patient from a nursing supply storage area or somewhere else other than the pharmacy or central filling station and therefore does not have information encoded on an electronic label by the pharmacy or central filling station. Also, in some situations, it is necessary to modify the contents of a medical fluid container. For example, one or more therapeutic agents, such as one or more drugs, may be injected through one or more fluid access regions 141 into the medical fluid container, thereby changing its contents. A data input pad on or associated with the infusion pump or a separate data-entry device (e.g., a laptop computer or other device) can be used by a healthcare practitioner or patient to transmit information to the electronic label to note a change in the contents of the medical fluid container and/or to note a change in any other information on the onboard label.

In some embodiments, custom compounded bags, syringes, or vials can be labeled during or after the fill process; however, in some embodiments, off-the-shelf, standard, or non-customized bags, syringes, or vials can be labeled before or when dispensed from a medication cabinet or from any other area where the medications are stored. A healthcare practitioner or patient at home may manually mix the bag (without a filling device) and print or encode the label, using a nearby computer, which is then affixed to the container.

Figure 3:
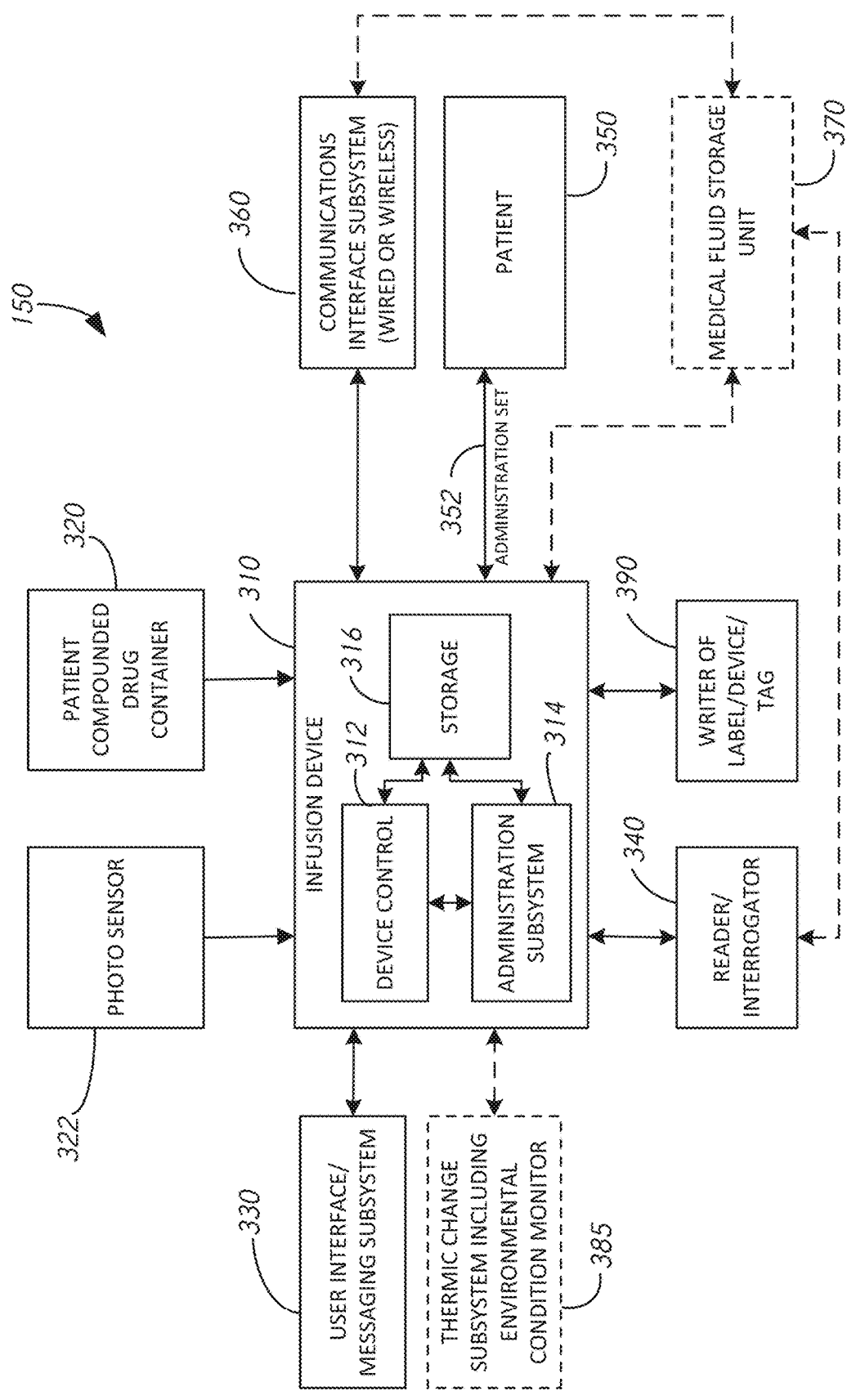
FIG. 3 is a diagram illustrating an example patient infusion system such as shown in FIG. 1B.

FIG. 3 is a block diagram illustrating a medical device system or infusion system 150 in some embodiments used in a hospital environment. In some embodiments, the medical device system is a system that can be used in a residential setting.

IV fluids/medications in a container 320 can be administered to a patient 350 through the infusion system 150 shown in FIG. 3. While the embodiments shown in FIGS. 1 and 2 may utilize barcodes and a barcode reader as means for providing and inputting or reading machine readable information for identification or other purposes, those skilled in the art will appreciate from this description that other means for providing and reading information can be utilized. Machine readable information can be provided by a near field communications (NFC) or radio frequency identification (RFID) tag, device, transmitter, or transponder and read by a radio frequency receiver or transceiver. Human biometric data, including but not limited to skin/fingerprints, retina patterns, voice, etc. can be recognized by an appropriate scanner or receiver. An input device or identification receiver adapted to "read" or recognize such indicia can be provided.

The IV fluids/medications in containers such as drug container 320 can be given new or supplemental label(s) with a unique infusion order identifying tag by the pharmacist. In particular, the drug container specific information can include patient identification information, such a patient name, patient number, or medical record number for which the medication has been prescribed, medication identification information, such as a medication name of the medication or solution within the IV bag or container 320, information which can be created or assigned at the hospital, medical device delivery information, such as the operating parameters to use in programming an infusion pump to deliver the medication to the patient 350, and/or medication order information, such as one or more of the above information items and/or other medication order information specific to a particular patient 350, and which may be a part of a medication order for a particular patient. The IV fluids/medications in containers 320 can be supplied to hospitals by various vendors, with preexisting unique identifiers which include medication information and other information, such as National Disease Center (NDC) code, expiration information, drug interaction information, and other information.

As shown in FIG. 3, the medical device system 150 (for example, an infusion system) and a remote central server 112 (FIG. 1) are coupled by a computer network 152, allowing the server and infusion system to communicate with one another using a communications interface subsystem 360. The communications interface subsystem 360 may be wired or wireless and is connected to an infusion device 310. The server 112 could be located in the hospital, at a location away from the hospital, at a manufacturer's facility, in another hospital, or anywhere else, as desired. The infusion system 150 includes a user interface and messaging subsystem 330, allowing a user (e.g., a doctor, nurse, technician, patient, etc.) to monitor and/or operate the infusion system 150. One embodiment of a user interface will be described below in conjunction with FIG. 12. The user interface 330 may include displays, key pads, touch screens, buttons and knobs, audio indicators, etc.

Updates from the server 112 may also be transferred to the infusion system 150 using a physical storage medium (e.g., a NFC or RFID label.), rather than using the network. The NFC or RFID label may be read by the reader or interrogator 340 that is connected to or internal to or integrated within the infusion device 310. An example of a suitable reader is the RFIDeas pcProxPlus. The updates may include a particular infusion program identified in the physician's order, obtained via the physician order system 120 (FIG. 1), for a particular patient 350. The label can include any information useful in the administration of medical fluid to a particular patient, including: security information and/or data derived from one or more onboard sensors regarding the product and/or its users to resist tampering or unauthorized removal or modification of the fluid; weight, specific gravity, and/or one or more other characteristics of the fluid to verify its contents; and/or present temperature and/or past temperature history of the fluid or its container. Also, a variety of communication networking methods could be used to accomplish the transfer depending on the networking infrastructure available; for example, Ethernet, Wi-Fi and cellular networks along with NFC and RFID could all be used for this purpose.

FIG. 3 also shows several subsystems of the infusion system 150. The communications interface subsystem 360 facilitates communications between the infusion system 150 and the server 112, as well as between the infusion system 150 and other devices. A device control subsystem 312 controls the operation of the infusion device 310, as well as the user interface 330. An administration subsystem 314 controls the infusion program for infusion of the medication in the patient drug container 320 for the current patient 350 through an administration set 352. The administration subsystem 314 operates in conjunction with the device control subsystem 312. The infusion device 310 also has a storage 316 in communication with the device control subsystem 312 and the administration subsystem 314. In the example of FIG. 3, the storage 316 may utilize flash memory and store installed software, configuration files, and updates. When updates are downloaded, they are cached and installed. At the same time, the current software and configuration files are cached, and are available to the system in the event that an update fails. This way, the medical device can return to the operating state that it was in prior to an attempted update. Also note that the storage, as described above, is merely an example. More or less storage could be used. Also, any desired type of storage medium could be used, besides flash memory. For example, the storage locations could use hard drives, solid state drives, or any other type of non-volatile memory.

In certain embodiments, after a new infusion program is read from the NFC or RFID label, a nurse (in a clinical setting) or the particular patient (in a residential setting) reviews the infusion program for the patient and confirms the program as being correct to initiate the infusion of the patient. The medication in the drug container 320 is infused by the infusion device 310 under control of the new infusion program obtained from the NFC or RFID label via the interrogator 340 into the patient 350 through the administration set 352. A photo sensor 322 tracks the level of the medication in the drug container 320 such that when the infusion is completed, a volume and/or weight of the infused medication can be derived and reported to the central server 112. In some embodiments, the weight of the medical fluid container can be converted by the processor into a volume based upon a known fluid density.

In some embodiments, whether residential, clinical, hospital, or otherwise, a pre-use medical fluid storage unit 370 can be provided that is configured to maintain safe environmental conditions, such as storing temperature, until the medical fluid is used. The pre-use medical fluid storage unit can be part of the infusion system 150 (either integrated into the same physical unit or provided as two separate units within the same infusion system). In some embodiments, the medical fluid storage unit 370 may be connected with the infusion device 310. In some embodiments, the medical fluid storage unit 370 may be connected with the interrogator 340 and the communications interface subsystem 360.

In some embodiments, a thermic change subsystem 385 can perform an operation (e.g., heating or cooling of the medical container or medical fluid) to bring the current temperature of the fluid to the correct dispensing temperature and then monitor the temperature during administration of the fluid to ensure it remains compliant and to make appropriate thermic adjustments. The thermic change subsystem 385 can be part of the infusion system 150 (either integrated into the same physical unit or provided as two separate units within the same infusion system).

If the infusion system 150 is not already equipped with the latest appropriate version of a hospital-established drug library, one or more updates or revisions or replacements of the drug library can be loaded into the infusion system 150. The hospital-established drug library may be maintained in a separate process undertaken by a biomedical engineer or the pharmacist to place limits on the programming of the infusion system 150, as well as other infusion pump operating parameters such as default alarm settings for air in the line, occlusion pressure, etc. The drug library can provide acceptable ranges or hard and/or soft limits for various drug delivery parameters in the infusion system 150. The drug library may also provide information to enable the device to verify the temperature lifecycle and reject the infusion if the medication has failed to maintain temperature during transportation and/or storage, to verify that the medication has not become adulterated or modified and reject the infusion if it has become so, and to verify the specific gravity or other weight analog and reject or notify the user or other information system if the current fluid weight has fallen out of range of the originally-identified or compounded weight when the fluid container was filled. Such a weight measurement system, in some embodiments, may include a hard equivalence comparison, a tolerance equivalence comparison (+/−), and/or a tolerance based on age (+/− per X unit of time elapsed since compounded). Further, such comparisons and/or the determination of whether to reject a particular medical fluid or fluid container may be based on the device identifying the material of the fluid container such that evaporation in PVC or other plastics allows for a different comparison rule than does glass or other impenetrable container.

One or more new versions, patches, or software updates of the infusion system's internal operating system software can also be loaded into the infusion system 150. The infusion settings or delivery parameters are read from the label on the container 320 and are entered into the storage 316 of the infusion device 310. In this way, the infusion device settings can automatically populate the programming screen(s) of the infuser, just as if a caregiver had entered the information and settings manually. An infusion device screen populates with the name of the drug and drug concentration based on the drug library index number, patient weight (if applicable), rate, VTBI, and duration (and in some embodiments only two of the last three variables are typically sent because the infusion device 310 can calculate the third from the other two). At this point the caregiver may manually enter any additional infusion settings or optional information that was not included in the label information. In some embodiments, it is not required for the caregiver to manually input any information regarding the fluid to be infused, the manner of administration of the fluid, and/or the patient, because all necessary information is included on the electronic label.

Figure 12:
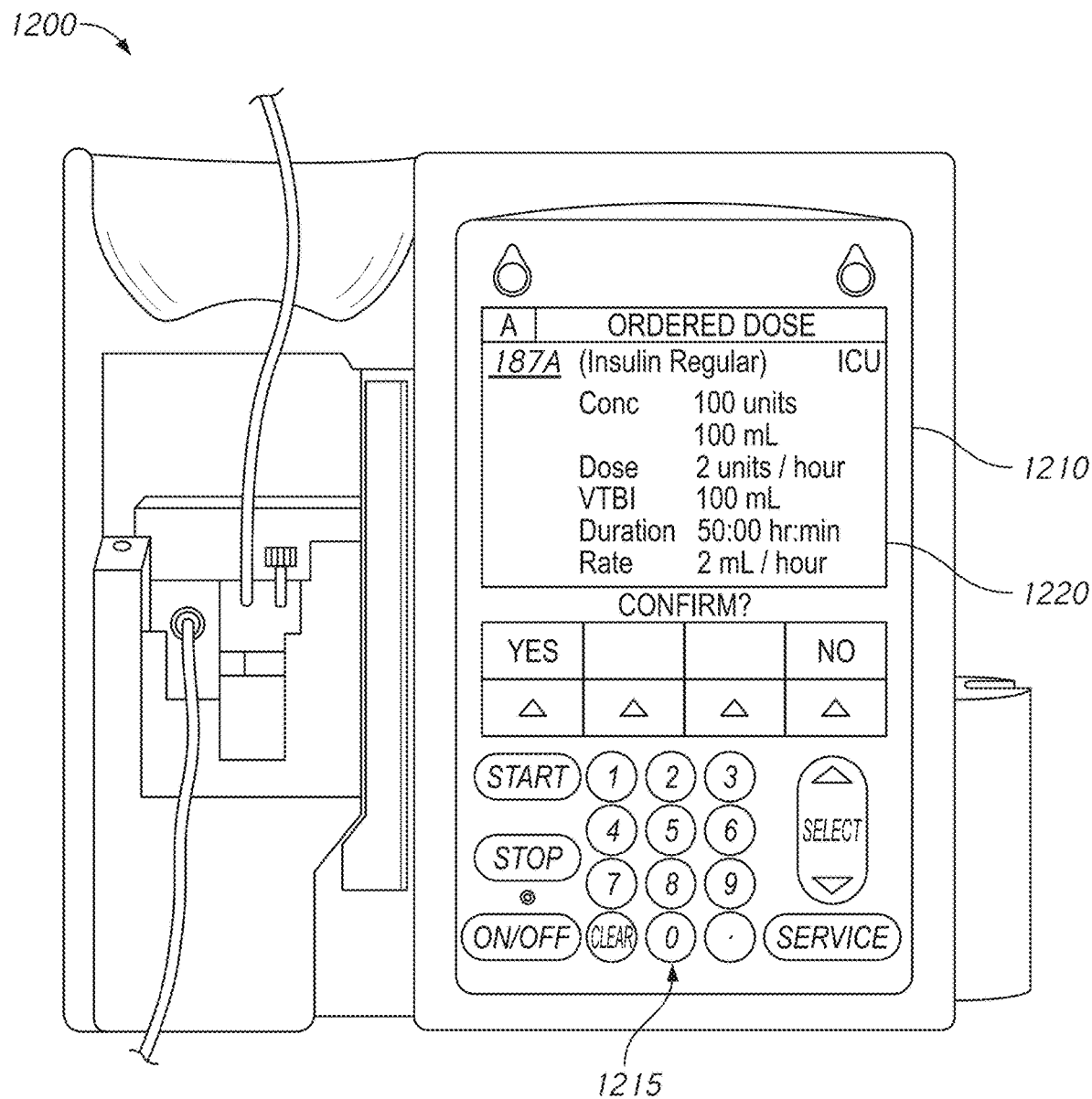
FIG. 12 is a diagram illustrating a front view of an example medical infusion device with a display and user interface, where the medical device is displaying example infusion settings.

The infusion system 150 then prompts the caregiver to start the infusion by pressing a start button. When the caregiver presses the start button, a confirmation screen with the infusion settings programmed is presented to the caregiver for confirmation, such as seen in FIG. 12. When the caregiver presses a button to confirm, the infusion system 150 will begin delivering fluid according to the programmed settings. In certain embodiments, the infusion system 150 sends a status message to the central server 112 indicating that the infusion system 150 was successfully auto-programmed, confirmed and started by the caregiver, and is now delivering fluid. The central server 112 may continue to receive logs and status messages wirelessly from the infusion system 150 periodically as the infusion progresses or when alarms occur.

In certain embodiments, the infusion system 150 includes a writer or printer 390 of a machine readable label/device/tag. The writer 390 includes the ability to write changes to the label so that, in the event of further transport, the label can act as the source of information for the medical fluid rather than an external source.

Figure 4:
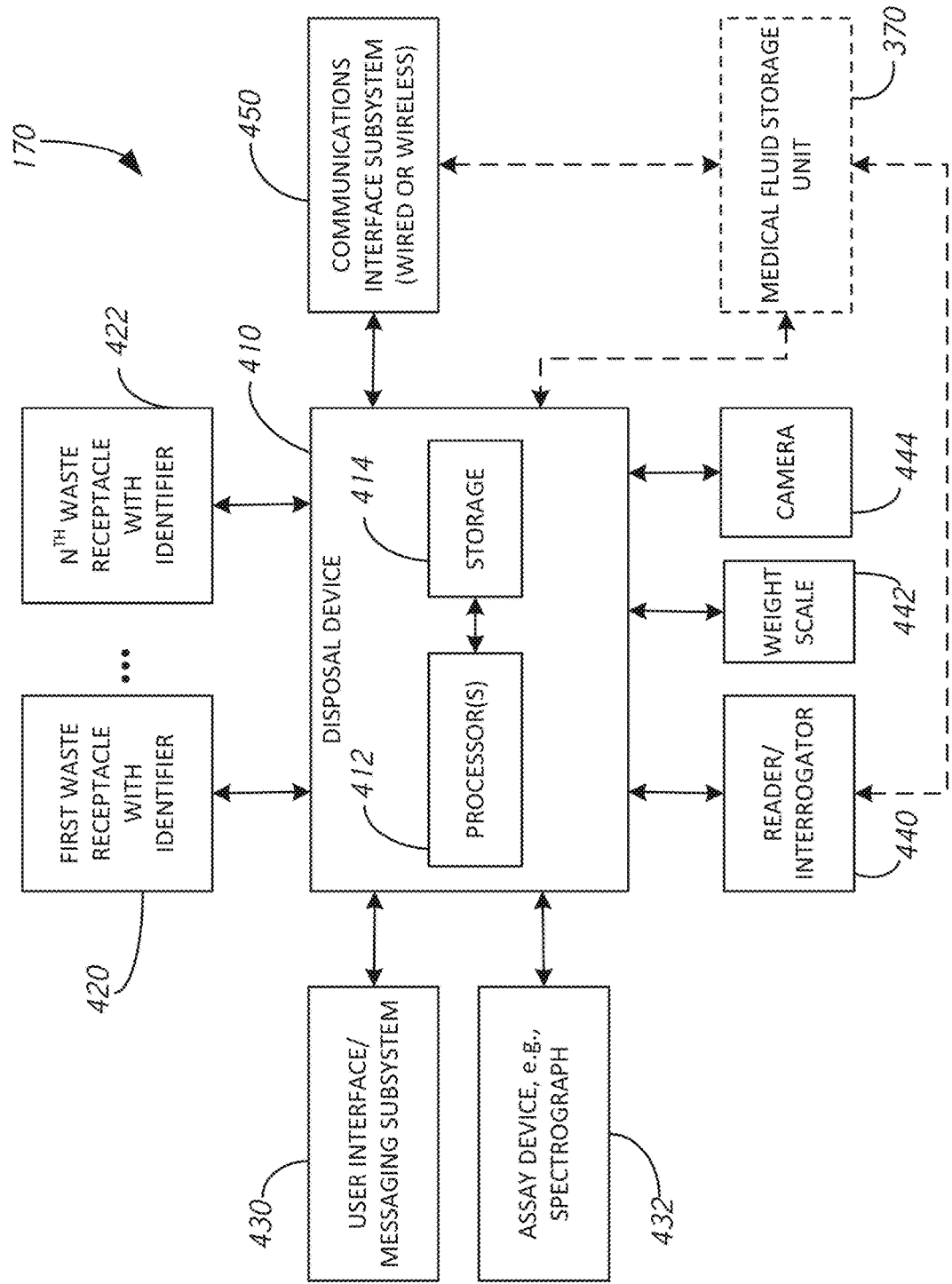
FIG. 4 is a diagram illustrating an example disposal system such as shown in FIG. 1B.

FIG. 4 illustrates an example disposal system 170 such as shown in FIG. 1. A disposal device 410 includes one or more electronic processors 412 and an electronic storage 414 for controlling multiple subsystems and processing and storing of data received from several subsystems. A first waste receptacle 420 with a first identifier is in data communication with the disposal device 410 for securely disposing of used patient medical waste, such as the drug container 160 (FIG. 1). In certain embodiments, multiple waste receptacles are included in the disposal system 170, such as an $n^{th}$ waste receptacle 422 with an $n^{th}$ identifier in data communication with the disposal device 410.

A user of the disposal device, such as a nurse or other clinical personnel, may interact with the disposal device 410 via a user interface/messaging system 430 in communication with the disposal device 410. For example, in some embodiments, the user interface/messaging system 430 may perform the following steps and/or interact with a user in the following ways: (1) verify a user's identity (e.g., by communicating electronically with an electronic badge, an RFID or NFC transponder, by capturing an image with a camera of a user's physical face or fingerprint or other feature, or in some other way); (2) read an item of information from a label on the fluid container; (3) instruct a user to place the fluid container or the fluid from the container in a disposal receptacle; (4) repeat steps (2) and (3) for additional items; (5) verify a user's identity again in a close-up procedure; and/or (6) display a completion message and receive the fluid or fluid container into the receptacle in a manner that prevents withdrawal of the fluid or fluid container without authorization. As with all steps or methods described or illustrated in this patent application, any part may be omitted, performed alone, and/or combined with any other steps or methods.

The disposal system 170 and the remote central server 112 (FIG. 1) are coupled by the computer network 152, allowing the server and disposal system to communicate with one another using a communications interface subsystem 450. The communications interface subsystem 450 may be wired or wireless and is connected to the disposal device 410. The NFC or RFID label on the used medical container 160 (or other used medical product) may be read by the reader/interrogator 440 that is connected to the disposal device 410. In addition, the reader/interrogator 440 may be configured to obtain and record or transfer (to the onboard label and/or the medical records system) the identity of any or all persons who have been temporarily or permanently associated with the medical fluid container 140, such as the physician or other healthcare provider who ordered the patient infusion, the pharmacy technician or other healthcare provider who compounded or filled the medical fluid bag 140, the orderly or other healthcare provider who transported the medical fluid bag 140 from the compounding or filling station to the patient infusion area or to or from any other area, the nurse or other healthcare provider who attended to the administration of the medical fluid from the medical fluid container to the patient, the patient who received the infusion, and the orderly or other healthcare provider who transported the used or partially used medical fluid container from the patient infusion area to the disposal site. For example, in some embodiments, the reader/interrogator 440 can be configured to read a badge, identification card, RFID label, bar code, or other identifier of one or more of such persons and then transmit one or more components of information about the identify of any of such persons, the time of any of such occurrences, the location of any of such occurrences, and/or one or more attributes (e.g., weight, appearance, contents, etc.) of the medical fluid container at the time of any of such occurrences.

A weight scale 442 can be in communication with the disposal device for weighing of the used medical container 160 (or other used medical product if appropriate) so as to determine the weight of any used medication along with the container. In some embodiments, a comparison of information or features can be calculated, recorded (on the onboard label and/or on the medical record system), and/or reported over time. For example, the weight of the used (including partially used) medical fluid container can be determined and recorded at various points in time and location and compared with the original weight of the container and medication minus the infused medication. A camera 444 is also in communication with the disposal device 410. The camera 444 can be used to record images at any stage of the disposal process. In certain embodiments, the camera 444 captures an image of the label affixed on the used medication container of the medicine or of other medical waste and/or captures an image of the person performing the disposal.

In certain embodiments, an assay device 432, such as a spectrograph (for example), or any other suitable device for obtaining or calculating one or more pieces of information about the medical fluid or medical fluid container, is provided in communication with the disposal device 410. The assay device 432 may be used to perform an analysis of the fluid container or any remaining medical fluid, such as medication or drug to confirm that the medical fluid in the medical fluid container is indeed what is specified on the label. The results can be provided to the central server 112 for matching to the original medicine or drug having the particular label. Any or all of the items of information that are identified or compared or calculated or captured, either individually or combined in any collection or aggregation of data, can be recorded, stored, and/or provided to the central server 112 and/or written onto the onboard label of the medical fluid container and/or transmitted to the medical record system for later use or reporting. For example, after the fluid container has been inserted into and/or secured within the disposal receptacle, and is beyond the reach of or access by the user, the fluid container can be penetrated and/or the fluid contained therein can be accessed by the assay device 432 to determine one or more physical, optical, or chemical characteristics of the fluid or fluid container. An example of the assay device 432 is the PharmID Verify device.

In some embodiments, whether residential, clinical, hospital, or otherwise, the disposal system 170 can include the pre-use medical fluid storage unit 370 that is configured to maintain safe environmental conditions, such as storing temperature, until the medical fluid is used. The pre-use medical fluid storage unit can be part of the disposal system (either integrated into the same physical unit or provided as two separate units within the same disposal system). In some embodiments, the medical fluid storage unit 370 may be connected with the disposal device 410. In some embodiments, the medical fluid storage unit 370 may be connected with the interrogator 440 and the communications interface subsystem 450.

In some embodiments, the disposal system 170 can help to make the medical record system more complete and/or can help to recover expenses to be charged to a patient in a healthcare setting that may otherwise go unreported or uncharged by generating and recording on the label one or more items of information or reports at the infusion and/or disposal stages that may not have been previously recorded in the medical record system. For example, in many situations, a medical fluid container is urgently required for an immediate patient need, without being produced and tracked through the hospital pharmacy or in any other system, which may lead to a failure to record the administration of such medical fluid to the patient in the medical record system and/or a failure to charge the patient for such administration. By enabling the infusion pump to record on the label affixed to the medical fluid container the information relating to the patient, the medication, and/or the administration of the medical fluid and then ultimately transmitting this information to the medical record system from the infusion pump or from the disposal system, the patient's records can be made more complete and the recovery of patient expenses can be increased.

Figure 5:
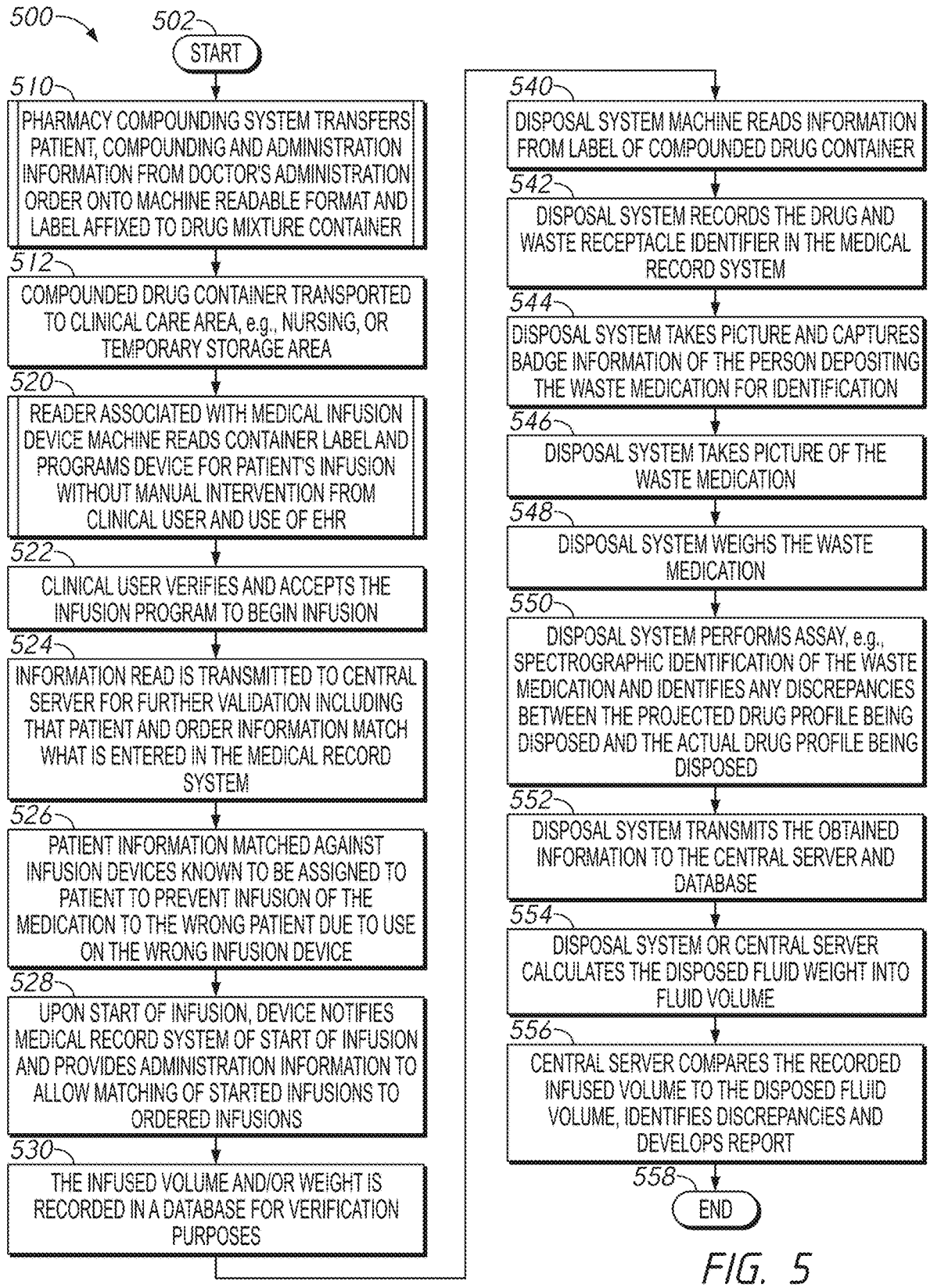
FIG. 5 is a flowchart of an example algorithm or process for infusion in a clinical setting and secure disposal such as may be performed using the example system shown in FIG. 1B.

FIG. 5 is a flowchart of an example algorithm or process 500 for infusion in a clinical setting and secure disposal such as performed using the example system shown in FIG. 1. The process may be performed by one or more of the processors associated with the pharmacy filling or compounding system 130, the infusion system 150, the disposal system 170 and the central server 112, examples of which are shown in FIGS. 1-4. In certain embodiments, the steps may be performed in a different order and/or certain steps may be combined and/or omitted.

Beginning at a start step 502, process 500 includes a function, subroutine or sub-process 510 where the pharmacy filling or compounding system 130 transfers patient, filling or compounding and administration information from the doctor's administration order onto a machine readable format and a label is affixed to drug mixture container. Further steps of sub-process 510 will be described in conjunction with the steps shown in FIG. 7 below. Proceeding to a step 512, the drug container 140 is transported to a clinical care area, e.g., nursing, or a temporary storage area. Advancing to a function, subroutine or sub-process 520, the reader 340 associated with medical infusion device 310 machine reads the container label and programs the device 310 for patient infusion without manual intervention from the clinical user and without the use of an electronic health record (EHR). Further steps of sub-process 520 will be described in conjunction with the steps shown in FIG. 8A below.

Continuing at a step 522 of process 500, a clinical user verifies and accepts the infusion program to begin the patient infusion process. The infusion device 310 or pump may also verify one or more characteristics of the medical container or medical fluid in the container, such as the weight, specific gravity, or other weight analog, or any other characteristic of the medical container or medical fluid, to verify that the medical container or medical fluid is the same or has substantially the same characteristics as when it was filled, compounded, or otherwise prepared. If there is a clinically significant or material deviation outside of normal parameters in the one or more characteristics of the medical container or medical fluid, the pump can alert the user, the attending healthcare professional, or an information system, such as via the user interface/messaging subsystem 330.

The medical container may also include one or more items of compliance data or compliance measuring devices, such as a time stamp, a timer, and/or one or more environmental sensors, such as a temperature sensor. The label may have encoded thereon acceptable ranges of time periods and environmental conditions in which the medical container can be transported, stored, and/or used. The infusion device 310 or pump can verify that the medical container or medical fluid has been properly transported and stored within the acceptable ranges of time and one or more environmental conditions. The pump can perform a thermic change operation (e.g., heating or cooling of the medical container or medical fluid) to bring the current temperature of the fluid to the correct dispensing temperature and then monitor the temperature during administration of the fluid to ensure it remains compliant and to make appropriate thermic adjustments. The pump may use encoded information and/or one or more timers and/or environmental sensors to verify that the container has not become adulterated.

Proceeding to a step 524, information read by the reader/interrogator 340 is transmitted to the central server 112 for further validation including that the patient and order information match what is entered in the medical record system 110. Advancing to a step 526 of process 500, patient information is matched against infusion devices known to be assigned to the patient to prevent infusion of the medication to the wrong patient due to use on the wrong infusion device. Proceeding to a step 528, upon start of the patient infusion, the infusion device 310 notifies the medical record system 110 of the start of infusion and provides administration information to allow matching of started infusions to ordered infusions so as to identify any discrepancies. In performing a customized course of infusion for a particular patient, the infusion system 150 is not required to communicate with or store information in the medical record system 110 or electronic health record, but can instead communicate or store all necessary information for the course of infusion through the label affixed to the medical fluid container 320. This includes the ability to write changes to the label so that, in the event of further transport, the label can act as the source of information for the medical fluid rather than an external source. For example, the name, volume, concentration, and/or weight of the infused drug, the name, volume, concentration, and/or weight of the residual drug, and the date, time and duration of administering the actual patient infusion, and/or patient identification information, may be electronically recorded on the label.

Continuing to a step 530, the infused volume and/or weight of the medicine or drug can be communicated to and/or recorded in the medical record system 110, central server 112, and/or database 114, for example, for verification purposes. Additionally, or alternatively, the infusion device 310 can communicate to the medical record system 110, central server 112, and/or database 114 that the infusion has been terminated at a specific stage (e.g., by reporting a particular infused volume over a particular infusion time) or that the infusion as prescribed has been completed. After step 530, the used container with any remaining medication, or other remaining medical product, is transported to a site having the disposal system 170 for secure disposal.

Proceeding to a step 540 of process 500, the disposal system 170 machine reads information from the label affixed on the used drug container 160 or on other medical waste products using the reader/interrogator 440, for example. Advancing to a step 542, the disposal system 170 records the drug and the waste receptacle identifier in the medical record system 110. Continuing at a step 544, the disposal system 170 takes one or more pictures and captures badge or identification card information of the person depositing the waste medication for identification and at a step 546, it takes one or pictures of the waste medication and container, and may include a picture of the label corresponding to the waste container and medication or other medical product. Proceeding to a step 548, the disposal system 170 weighs the waste medication and container or other medical product as appropriate. Moving to a step 550, the disposal system 170 performs an assay, e.g., spectrographic identification of the waste medication and identifies any discrepancies between the projected drug profile being disposed and the actual drug profile being disposed. In certain embodiments, the identification of discrepancies is performed by the central server 110 and/or may be performed by the disposal system 170. At a step 552, the disposal system 170 transmits the obtained information from the subsystems to the central server 112 and database 114. Continuing at a step 554, the disposal system 170 or the central server 112 calculates the disposed fluid weight into fluid volume, and at a step 556, the disposal system 170 or the central server 112 compares the recorded infused volume with the disposed fluid volume, identifies any discrepancies in view of the original volume and develops a report of the disposal process including any discrepancies. In certain embodiments, discrepancies and/or reports may be provided at the user interface/messaging subsystem 430 of the disposal system 170. Such reports are then reviewed by appropriate hospital officials periodically so as to identify any issues of drug abuse. Process 500 completes at an end state 558.

In certain embodiments, the disposal system may be configured to associate the identity of a person operating the disposal device with the unique identifier of the waste receptacle used for the disposing. The user may be required to present identification information in machine readable format (e.g., by presenting an identification badge) prior to executing the disposal workflow to ensure that he or she is an authorized user and/or to record the user's involvement, activity, or contact with one or more particular drug containers. A security authentication confirmation or denial may be provided visually and/or audibly to the user. Narcotic or other high risk medications may require more than one authorized user to present an authentication card or other identifying means, where the security authentication confirmation or denial may be provided visually and/or audibly to the user, including instructions on presenting subsequent user authentication identification and the success or failure thereof.

Figure 6:
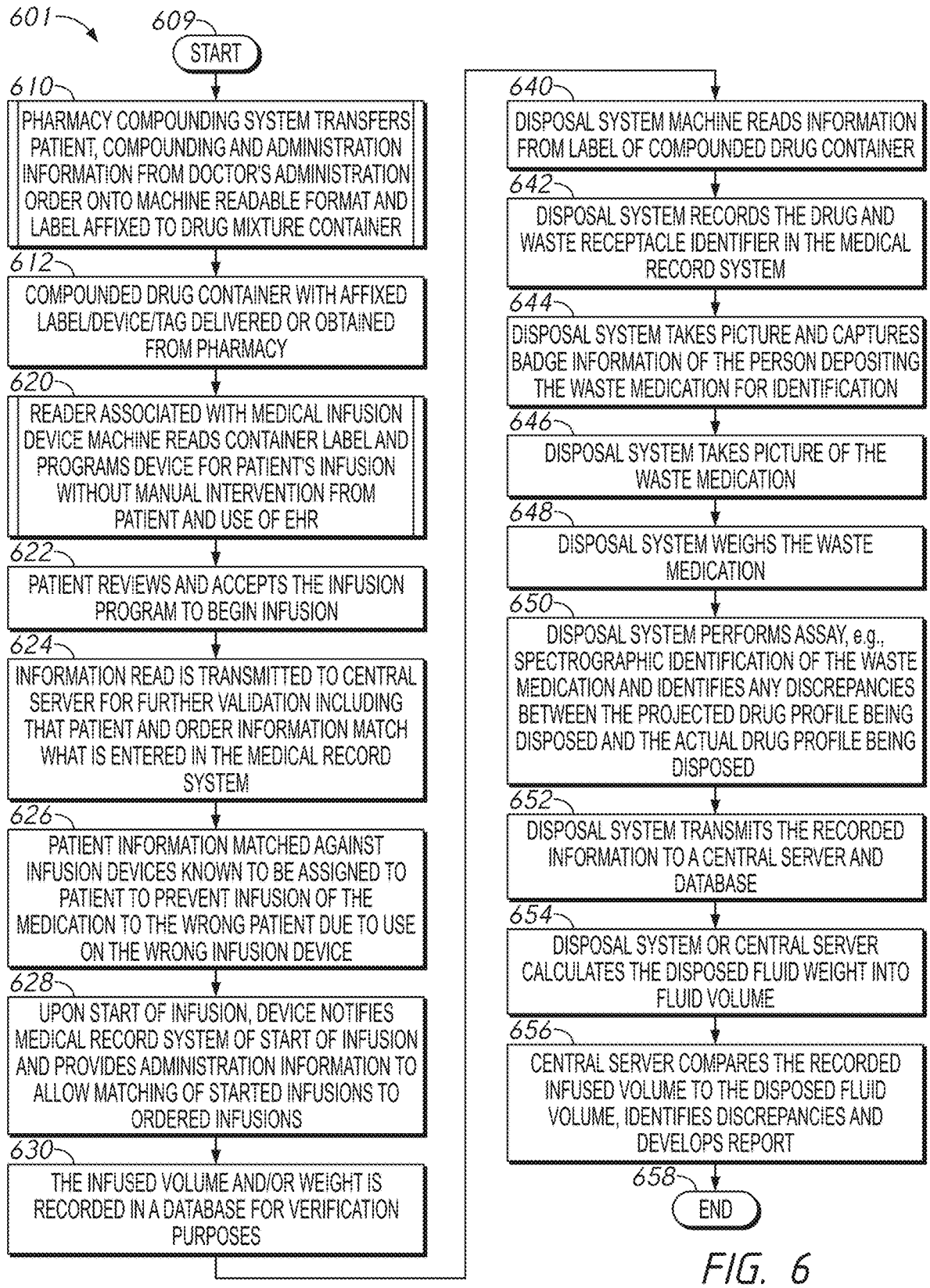
FIG. 6 is a flowchart of an example algorithm or process for infusion in a residential setting and secure disposal such as may be performed using the example system shown in FIG. 1B.

FIG. 6 is a flowchart of an example algorithm or process 601 for infusion in a residential setting and secure disposal such as performed using the example system shown in FIG. 1. The process may be performed by one or more of the processors associated with the pharmacy filling or compounding system 130, the infusion system 150, the disposal system 170 and the central server 112, examples of which are shown in FIGS. 1-4. In certain embodiments, the steps may be performed in a different order and/or certain steps may be combined and/or omitted.

Beginning at a start step 609, process 601 includes a function, subroutine or sub-process 610 where the pharmacy filling or compounding system 130 transfers patient, filling or compounding and administration information from the doctor's administration order onto a machine readable format and a label is affixed to drug mixture container. Further steps of sub-process 610 will be described in conjunction with the steps shown in FIG. 7 below. Proceeding to a step 612, the drug container 140 is either delivered to a patient's residence by a delivery service, which may or may not be affiliated with the pharmacy preparing the medication, or may be picked up at the pharmacy by the patient or a patient representative. Advancing to a function, subroutine or sub-process 620, the reader 340 associated with medical infusion device 310 machine reads the container label and programs the device 310 for patient infusion without manual intervention from the patient and without the use of an electronic health record (EHR). Further steps of sub-process 620 will be described in conjunction with the steps shown in FIG. 8B below. Continuing at a step 622 of process 601, the patient verifies and accepts the infusion program to begin the infusion.

The remaining steps of process 601 are similar to those of process 500 shown in FIG. 5 and, therefore, are not further described here. However, after step 630, the used container with any remaining medication, or other remaining medical product, is either picked up by a delivery service from the patient's residential setting and delivered to a site having the disposal system 170, or the patient or the patient's representative delivers the used container with any remaining medication, or other remaining medical product, to the site having the disposal system 170 for secure disposal. As with all flowcharts, algorithms, or methods illustrated and/or described in this specification, any step(s) can be performed in any suitable order and are not constrained to the order provided in the examples, and any step(s) in one figure or passage can be used separately or combined with any step(s) of another figure or passage.

Additionally or alternatively, in a residential system, a disposal system can be provided with electronic networking connectivity within the patient's residence. In some embodiments, whether residential, clinical, hospital, or otherwise, the pre-use medical fluid storage unit 370 can be provided that is configured to maintain safe environmental conditions, such as storing temperature, until the medical fluid is used. The pre-use medical fluid storage unit can be part of the disposal system (either integrated into the same physical unit or provided as two separate units within the same disposal system). The storage unit can provide separate connectivity and read/write communication with the label on the fluid container and/or the medical record system 110, central server 112, and/or database 114.

Figure 7:
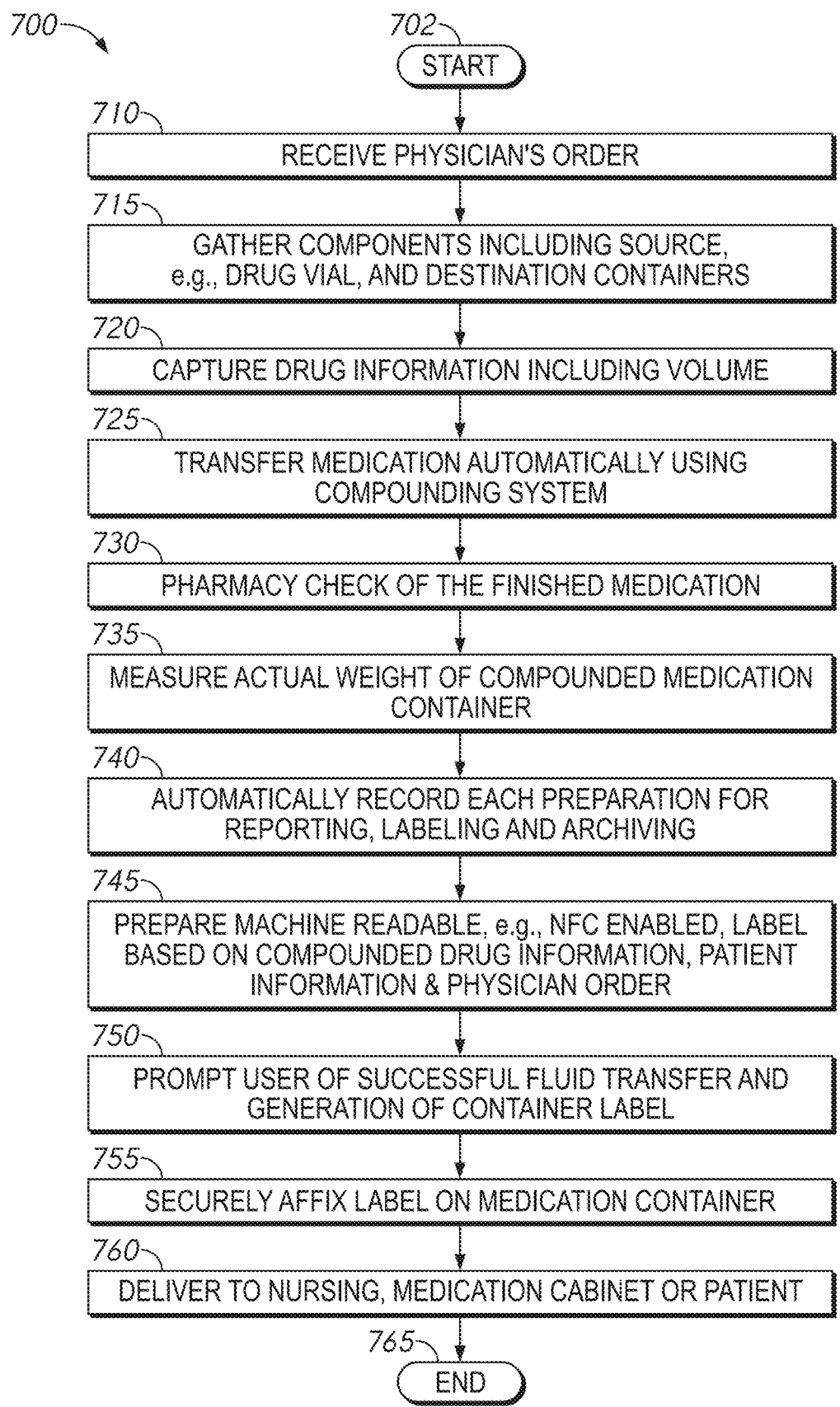
FIG. 7 is a flowchart of an example algorithm or process for operation of the filling or compounding system such as may be performed using the example system shown in FIG. 2.

FIG. 7 is a flowchart of an example algorithm or process 700 for operation of the filling or compounding system such as performed using the example system shown in FIG. 2. In certain embodiments, the process 700 may be performed by one or more of the processors associated with the pharmacy filling or compounding system 130 and the central server 112, examples of which are shown in FIGS. 1-2. In certain embodiments, the steps may be performed in a different order and/or certain steps may be combined and/or omitted.

Beginning at a start step 702, process 700 advances to a step 710 where the pharmacy filling or compounding or fluid transfer system 130 receives the physician's order for the patient medication. In certain embodiments, the order may be received from the medical record system 110 or from the physician order system 120. Proceeding to a step 715, the pharmacist or technician gathers the needed components including source, e.g., drug vial 262, and destination container(s) 264. Advancing to a step 720, the filling or compounding system captures drug information including volume. At a step 725, the filling or compounding system 130 transfers the medication automatically into the destination container 264. Moving to a step 730, the pharmacist checks the finished medication for completeness and accuracy in view of the order. Continuing at a step 735, the actual weight of the medication container is weighed using scale 282 and the results captured by the filling or compounding device 260.

Advancing to a step 740, the filling or compounding system 130 prepares a machine readable, e.g., NFC enabled, label based on the drug information, the patient information and the physician order for administration instructions. Upon completion of step 740, the user is prompted at a step 745 of the successful fluid transfer and generation of the label for the destination container 264. Proceeding to a step 750, the label is securely affixed to the destination medication container 264. In certain embodiments, the label is securely affixed manually by the pharmacist or technician. In certain embodiments, the filling or compounding system 130 may automatically affix the label onto the medication container 264. Continuing to a step 755, the filling or compounding system 130 automatically records each preparation for reporting and archiving, which, in certain embodiments, includes sending the information to the medical record system 110. Advancing to a step 760, the medication container 264 with the affixed label is transferred to the nursing department corresponding to the patient, to a secure medication area or cabinet, or to the patient (e.g., for residential infusion). The process 700 completes at an end state 765.

Figure 8A:
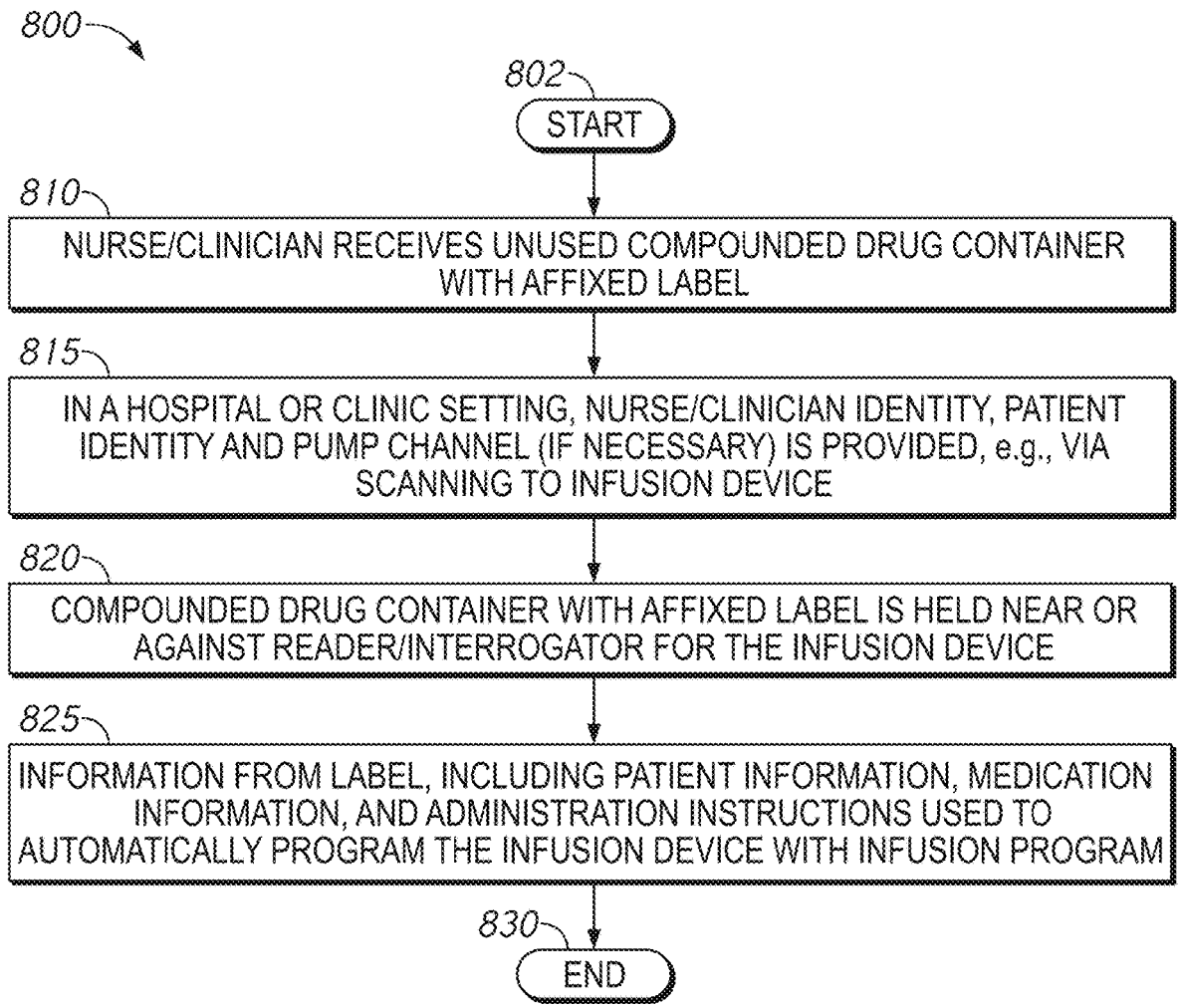
FIG. 8A is a flowchart of an example algorithm or process for programming of the infusion system such as may be performed in a clinical setting using the example system shown in FIG. 3.

FIG. 8A is a flowchart of an example algorithm or process 800 for programming of the infusion system 150 using an onboard label on a medical fluid container, such as performed in a clinical setting using the example system shown in FIG. 3. In some embodiments, the process 800 may be performed independently, without requiring any communication with a medical record system or an electronic health record. In certain embodiments, the process 800 may be performed by one or more of the processors associated with the infusion system 150 and the central server 112, examples of which are shown in FIGS. 1 and 3. In certain embodiments, the steps may be performed in a different order and/or certain steps may be combined and/or omitted.

Beginning at a start step 802, process 800 advances to a step 810 where the nurse or clinician receives an unused drug container 320 with an affixed label from the pharmacy or secure storage area. Moving to a step 815, in the hospital or clinic setting, an identity of the nurse or clinician, the patient and an infusion device pump channel (if necessary) is provided, e.g., such as via scanning using the reader/interrogator 340, to the infusion device 310. Advancing to a step 820, the drug container 320 with the affixed label is held near or against the reader/interrogator 340 such that the information encoded on the label is transferred to the infusion device 310. Continuing at a step 825, information from label, including patient information, medication information, and administration instructions is used to automatically program the infusion device with the infusion program for the patient according to the physician order. The process 800 completes at an end step 830.

In some embodiments, this method of programing the infusion device with the infusion program can provide enhanced patient safety and clinician workflow. Drug errors and manual steps can be diminished and time can be saved by automatically populating the infusion device with pharmacist vetted medication orders directly transferred from the label affixed to the medication container. This type of programming extends the benefits of integration beyond the initial infusion set-up to include much of what the healthcare provider does for infusion management, but in an integrated environment (e.g., handling new bags, rate changes, titrations, medications not in the drug library, and changes to the care area without needing to stop or restart the infusion device). Infusion documentation may capture infusion device settings, start and stop times, and titrations. In certain embodiments, a reader or interrogator in communication with an intravenous infusion pump can read the encoded information on a short range communication device on the liquid container transferred to a patient's bedside. The read information can be utilized to program an infusion course into the bedside intravenous infusion pump in communication with the first interrogator. The intravenous infusion pump can enable multiple infusions either concurrently or serially on one or more fluid input ports on one or more infusion sets. A subsystem may convert an infusion pump event into an audible and/or visual event to provide information to the user. The audible event may be a voice file or the audible event may be a sound or tone that is not a voice that provides meaningful instruction to the user. The encoded information on the short range communication device on the liquid container may be in contact with the interrogator for varying amounts of time to correspond to a desired fluid input port on the intravenous infusion pump (e.g., one second of contact may be equivalent to port 1 and five seconds of contact may be equivalent to port 2). The user may be required to present identification information in a machine readable format prior to executing the infusion workflow to ensure that he or she is an authorized user. The security authentication confirmation or denial may be provided visually and/or audibly to the user. Narcotic or other high risk medications may require more than one authorized user to present an authentication card, badge or other means. The security authentication confirmation or denial may be provided visually and/or audibly to the user, including instructions on presenting subsequent user authentication identification and the success or failure thereof.

Figure 8B:
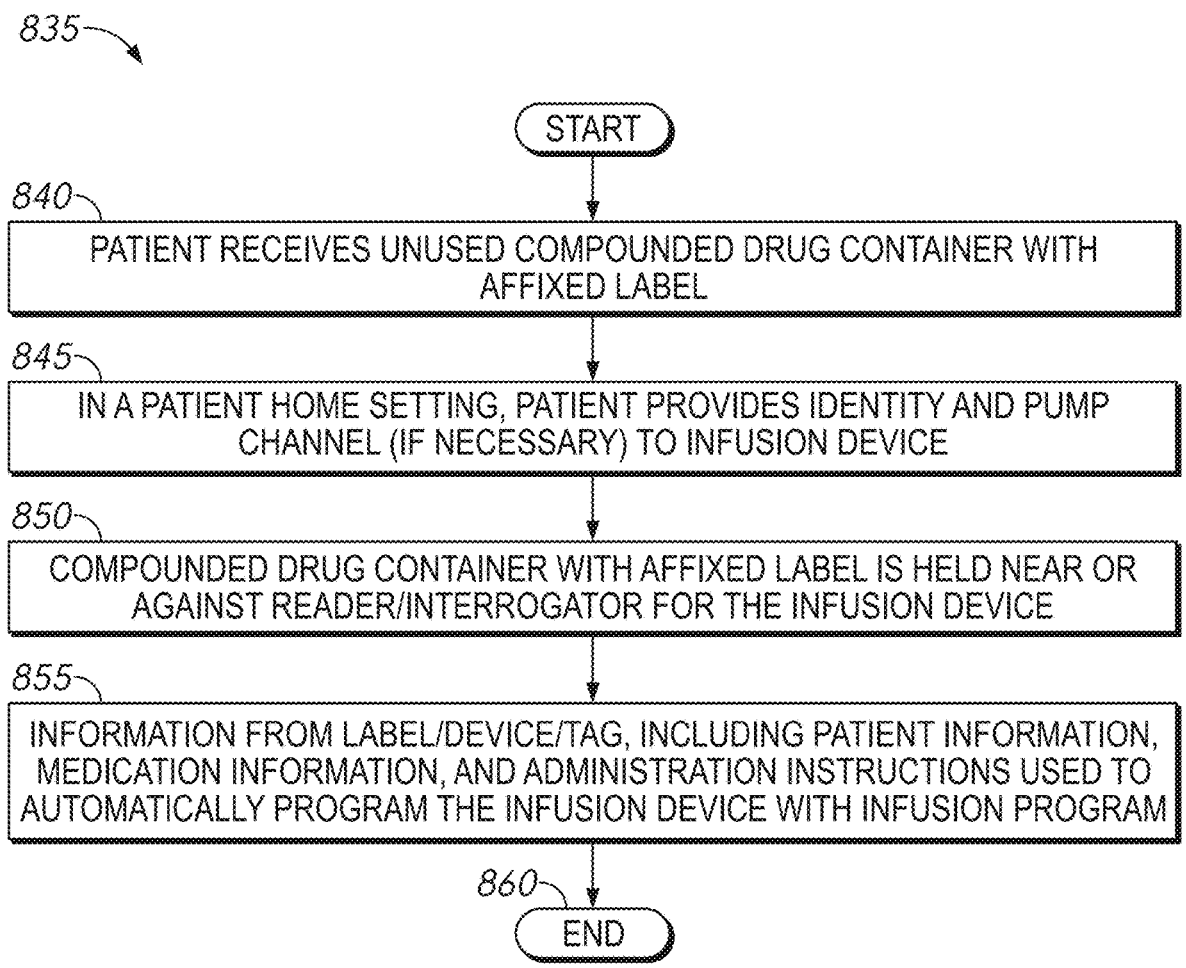
FIG. 8B is a flowchart of an example algorithm or process for programming of the infusion system such as may be performed in a residential setting using the example system shown in FIG. 3.

FIG. 8B is a flowchart of an example algorithm or process 835 for programming of the infusion system 150 such as performed in a residential setting using the example system shown in FIG. 3. In certain embodiments, the process 800 may be performed by one or more of the processors associated with the infusion system 150 and the central server 112, examples of which are shown in FIGS. 1 and 3. In certain embodiments, the steps may be performed in a different order and/or certain steps may be combined and/or omitted.

Beginning at a start step 838, process 835 advances to a step 840 where the patient receives an unused drug container 320 with an affixed label from the pharmacy via a delivery service or via pick-up by the patient or a patient representative. Moving to a step 845, in the patient residential setting, an identity of the patient and an infusion device pump channel (if necessary) is provided, e.g., such as via scanning using the reader/interrogator 340, to the infusion device 310. Advancing to a step 850, the drug container 320 with the affixed label is held near or against the reader/interrogator 340 such that the information encoded on the label is transferred to the infusion device 310. Continuing at a step 855, information from label, including patient information, medication information, and administration instructions is used to automatically program the infusion device with the infusion program for the patient according to the physician order. The process 835 completes at an end step 860.

Figure 9:
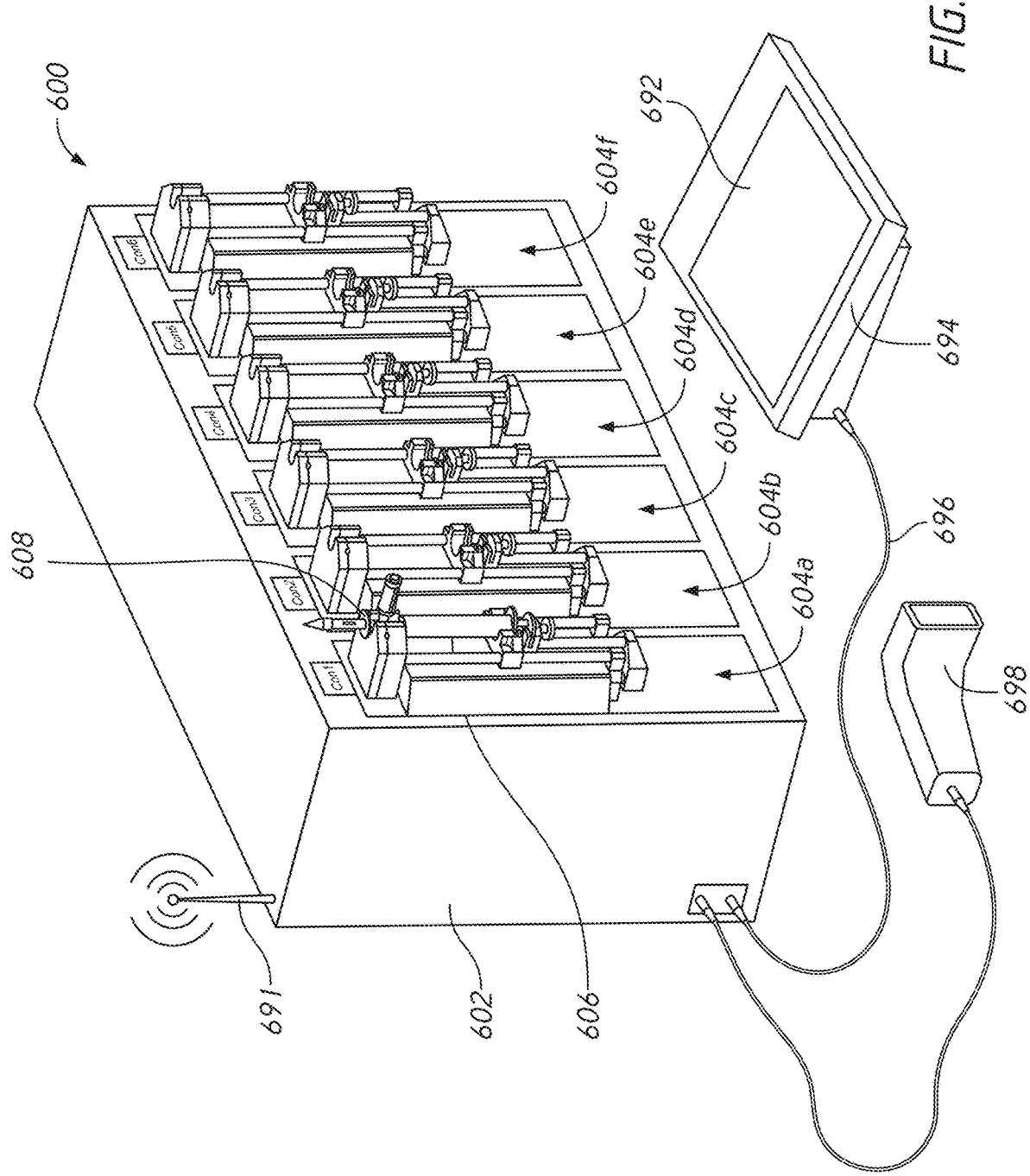
FIG. 9 is a diagram illustrating another example of an automated pharmacy filling or compounding system for transferring medical fluid.
Figure 10:
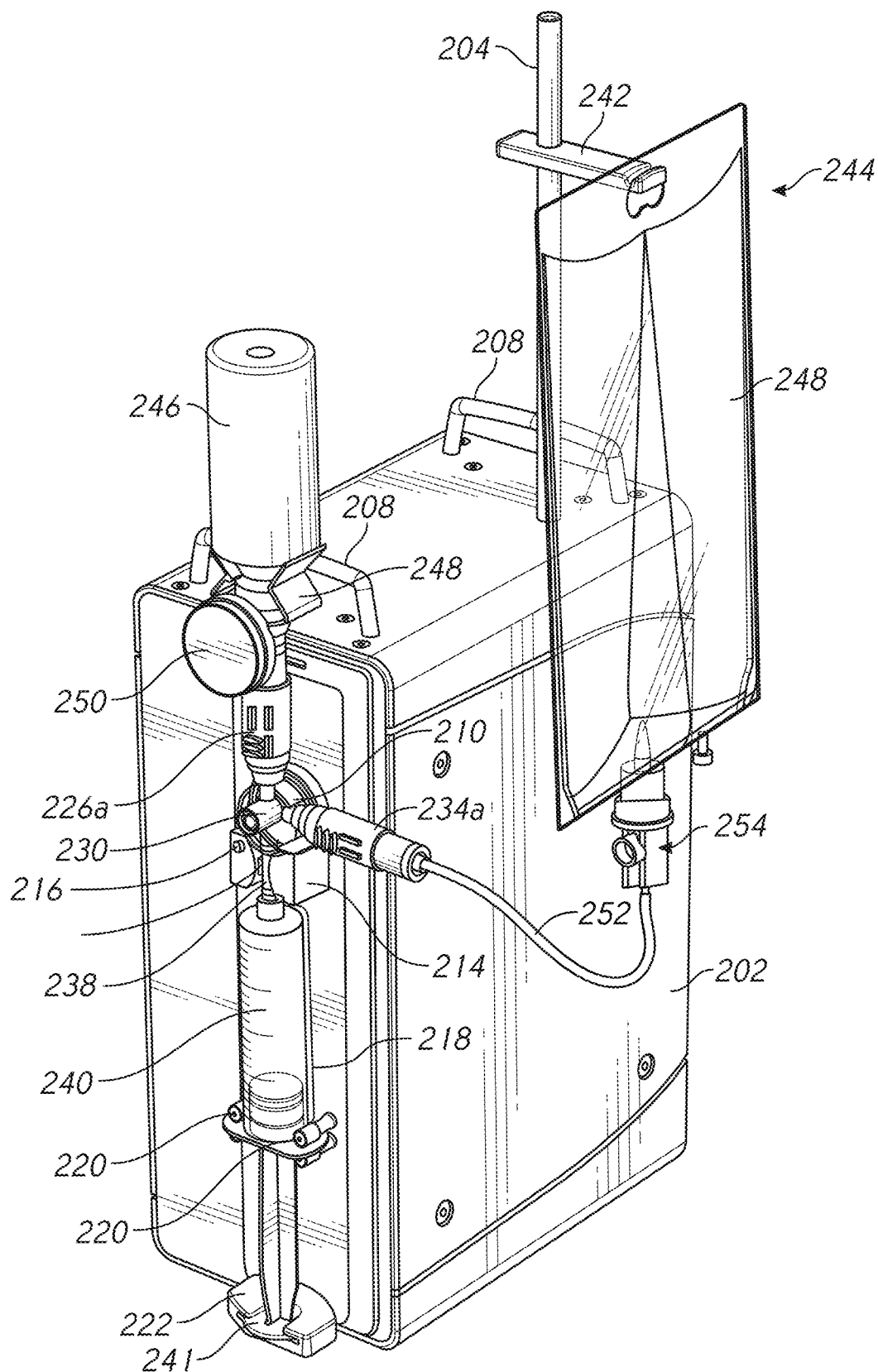
FIG. 10 is a diagram illustrating yet another example of an automated pharmacy filling or compounding system for transferring medical fluid.
Figure 11:
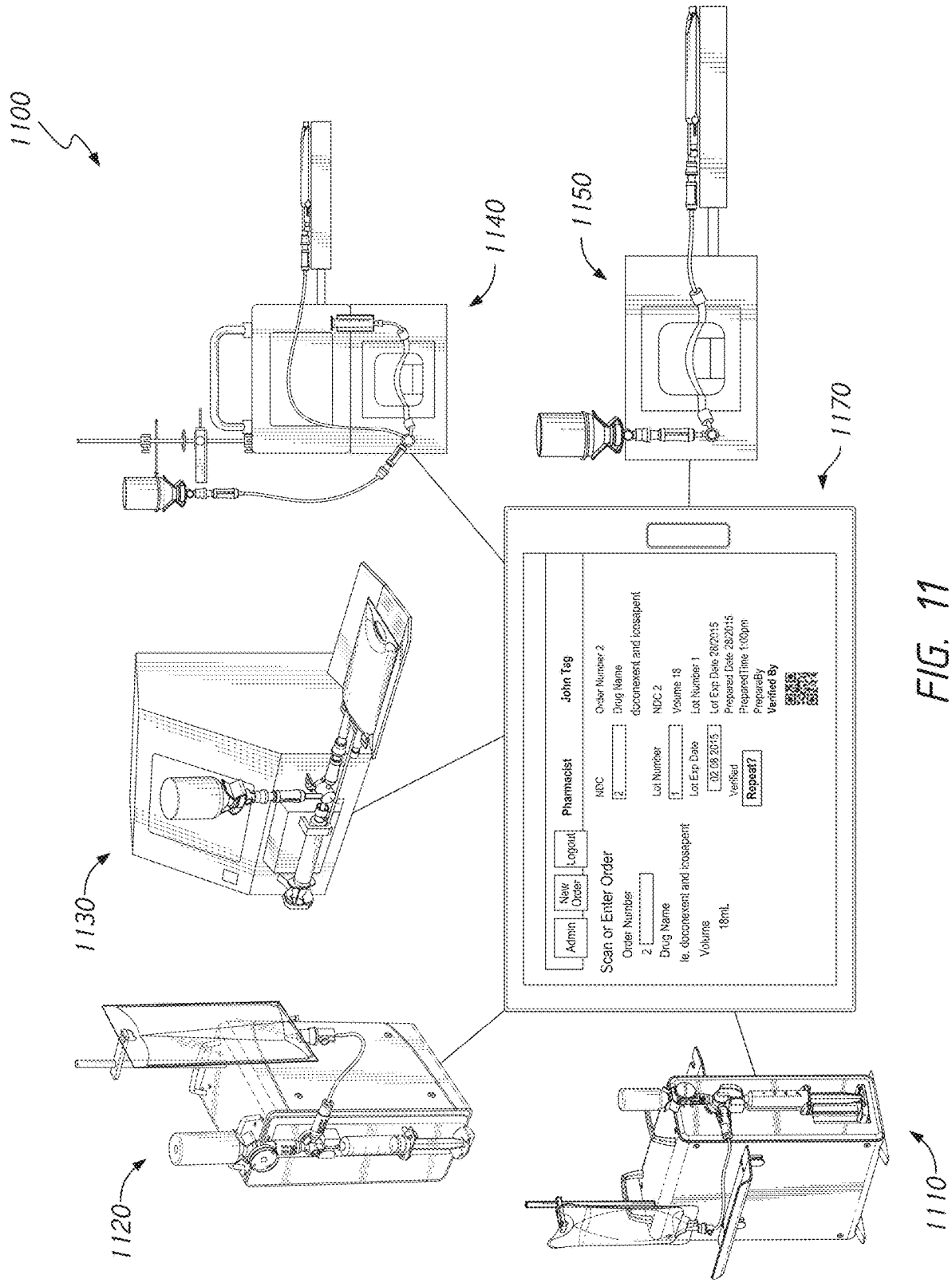
FIG. 11 is a diagram illustrating an example user interface configured to electronically communicate with different types of medical fluid transfer devices.

FIG. 9 is a perspective view of an automated system 600 for transferring fluid, which can be similar to or the same as other automated fluid transfer or pharmacy filling or compounding systems, such as shown in FIGS. 2, 10 and 11. The system 600 can include a base housing 602, and six transfer stations 604a-f, located on a front side of the base housing 602. In some embodiments, the system 600 can include a different number of transfer stations 604a-f (e.g., one, two, four, five, eight, or more transfer stations). In some embodiments, the transfer stations 604a-f can be distributed on multiple sides of the base housing 602. Transfer stations 604b-f are shown in an empty state having no syringe attached thereto. Transfer station 604a is shown having a syringe 606 and a connector 608 attached thereto. During operation, a vial (not shown) can be attached to the top of the connector 608 and an IV bag (not shown) can be placed in fluid connection with the connector 608 so that fluid can be transferred from the vial to the syringe 606 and then from the syringe 606 into the IV bag, as discussed above. Also, during operation, some or all of the transfer stations 604*a-f* can be equipped similarly to transfer station 604*a*. In some embodiments, multiple transfer stations 604*a-f* can operate simultaneously. In some embodiments, multiple transfer stations 604*a-f* can be placed in fluid communication with a single IV bag so that fluid from multiple vials can be combined into a single IV bag. In some embodiments, one or more of the transfer stations 604*a-f* can include a dedicated IV bag so that fluid from only a single transfer stations can be transferred into the dedicated IV bag.

In FIG. 9, the system 600 can include a user interface 692 for receiving information and commands from the user and for providing information to the user. The user interface 692 can be part of an external unit 694, or it can be integrated into or attached to the base housing 602. The user interface 692 can include, for example, a touch screen display. The user interface 692 can be in wired or wireless communication with the controller. In some embodiments, a cable 696 connects the external unit 694 to the base housing 602 and provides a communication link between the user interface 692 and the controller. In some embodiments, the controller can be contained in the external unit 694 along with the user interface 692 and the controller can send and receive signals to and from components (e.g., the motors) of the system 600 through the cable 696. The user interface 692 can be configured to receive instructions from the user regarding the amounts of fluids to be transferred by the transfer stations 604*a*-604*f*. The user interface 692 can deliver the instructions to the controller to be stored in a memory and/or used to actuate the motor(s) to transfer the desired amount of fluids.

In some embodiments, the system 600 can include a communication interface (shown schematically in FIG. 9 as antenna 691). The communication interface 691 can be configured to provide a communication link between the controller and a remote source, such as a remote terminal or an automated management system. The communication link can be provided by a wireless signal or a cable or combination of the two. The communication link can make use of a network such as a WAN, LAN, or the Internet. In some embodiments, the communication interface can be configured to receive input (e.g., fluid transfer commands) from the remote source and can provide information (e.g., results or alerts) from the controller to the remote source. In some embodiments, the remote source can be an automated management system which can coordinate actions between multiple automated fluid transfer systems, such as shown in FIGS. 2, 10 and 11.

The system 600 can also include a bar code scanner 698, in communication with the controller and/or memory. The bar code scanner 698 can be used to provide information about the system 600 to the controller and/or the memory. For example, the syringe 606 can include a bar code that identifies the size and type of the syringe 606. The user can scan the syringe 606 with the bar code scanner 698 and then scan a bar code associated with the transfer station 604*a* to inform the controller of the size of the syringe 606 that is attached to the transfer station 604*a*. Different sizes of syringes can hold different volumes of fluid when their plungers are withdrawn by the same distance. Thus, when the controller is tasked with filling the syringe 606 with a predetermined amount of fluid, the controller can determine how far the plunger is to be withdrawn to fill the particular type of syringe with the predetermined amount of fluid. The vials (not shown) can also include bar codes that indicate the type of fluid contained therein. The user can scan a vial and then scan the bar code associated with the particular transfer station the vial is to be installed onto. Thus, the controller can be aware of what fluids are controlled by which transfer stations to facilitate automated transfer of fluids. Other components of the system 600 can also include bar codes readable by the bar code scanner 698 for providing information about the components to the controller and/or memory. In some embodiments, the user interface 692 can be configured to allow the user to input data relating to the size of the syringe 606, the type of fluid contained in a vial, etc. instead of using the bar code scanner 698.

FIG. 10 is a front perspective view of another type of fluid transfer device 260 with Chemolock connectors 234*a*, 226*a* used, in this example. Any suitable type of connector or combination of connectors can be used. As illustrated in FIG. 10, the fluid transfer device 260 can be removably attached to the fluid transfer system 130, such as by using one or more of the supports on the fluid transfer system. For example, as shown in FIG. 10, a flat portion or end of the actuating stem 241 can be inserted into or coupled with a receiving region of the movable platform 222; one or more tabs on the syringe pump 240 can be positioned on or inserted between one or more of the protruding holders 220; the body of the syringe pump 240 can be received in the receptacle 218; the conduit 238 can be inserted into or on the sensor device 214, such as in a channel within the sensor device 214 that includes one or more sensors 215 (also referred to as one or more sensing regions 215; and/or the body of a fluid stopcock 230 can be positioned in or on or inserted into the attachment region 210 of the fluid transfer unit 200. In some embodiments, the fluid transfer device 260 can be removably retained on the fluid transfer system 130 by any suitable attachment structure, including a snap-fit, a friction fit, a clasp, a clip, a retaining arm or door, an elastic band, or any other attachment structure.

When the fluid transfer device 260 is removably attached to the fluid transfer system 130, a fluid-observation region on the conduit 238 can be positioned adjacent to or within an appropriate sensing distance from the one or more sensors 215. In the illustrated example, the fluid-observation region is at least a portion of the conduit 238 positioned between the fluid stopcock 230 and/or the intermediate container or pumping region, e.g., the syringe pump 240. In some embodiments, the fluid-observation region can comprise a portion of the conduit 238 positioned between the multidirectional flow-control valve (e.g., the fluid stopcock 230) and/or the intermediate container or pumping region (e.g., the syringe pump 240). In some embodiments, the fluid-observation region can be positioned in another position on the fluid transfer device, or there can be multiple fluid-observation regions located at a plurality of positions on the fluid transfer device.

In some embodiments, the one or more sensors 215 can be configured to determine whether there is liquid, gas (e.g., one or more bubbles), and/or a vacuum or partial vacuum, within a particular region or regions of the fluid transfer device. For example, the one or more sensors 215 can be configured to determine whether there is a medical fluid within at least a portion of the conduit 238 or whether there is a gas (e.g., ambient air or air bubbles) or a vacuum or partial vacuum within the conduit 238. In some embodiments, the one or more sensors 215 can determine whether there is a medical fluid within a portion of the conduit 238 or whether there is a gas (e.g., ambient air) or a vacuum or partial vacuum within a portion of the conduit 238. The one or more sensors 215 can be any suitable type of sensor, including but not limited to one or more acoustic sensors (e.g., ultrasonic sensors), infrared sensors, laser sensors, visual-spectrum optical sensors, motion flow sensors, or any other suitable sensors. One or more indicators 216, such as an indicator light or indicator speaker or other indicator, can be positioned on the sensor device 214 to indicate when the sensor device 214 is sensing a particular condition, such as when liquid is present in the fluid observation-region.

FIG. 10 also illustrates a fluid source container in the form in this example of an inverted vial 246 attached to a vial adaptor 248 that is in turn attached to an inlet connector in the form in this example of a male fluid connector 226a with a longitudinal locking mechanism. In some embodiments, the vial adaptor 248 comprises a filtered fluid inlet and/or outlet 250 and securing arms that are configured to securely receive the vial. FIG. 10 also illustrates a fluid destination container in the form in this example of an IV bag 244 attached to a conduit or hose 252 (in this example by way of a bag spike 254 or other fluid connection point) that is in turn attached to an outlet connector of the fluid transfer device. The outlet connector in FIG. 10 is in the form in this example of a male fluid connector 234a with a longitudinal locking mechanism. The IV bag 244 is suspended from a pole stand 204 by a support arm 242.

FIG. 11 illustrates a user interface 1170 that can be used with the fluid transfer system 130 in the form in this example of a remote tablet. The user interface 1170 can comprise a rechargeable internal battery, a touch-sensitive screen to enable user selection and input by way of the screen, and one or more additional or alternative user inputs, such as a button (as shown) or a knob or a slider or a rocking switch, or a rolling dial, or any other user input. The user interface 1170 can communicate electronically with one or more fluid transfer devices and/or with one or more patient and/or drug information storage devices or networks utilizing any suitable electronic protocols or electronic communicators. In some embodiments, the user interface 1170 is fixed to the fluid transfer device, such as being attached to or contained at least partially within the housing of the fluid transfer device.

The user interface 1170 can display or convey various items of information between a user and an electronic storage medium and/or can convey one or more executable instructions to a computer processor in the fluid transfer device 260, or to electromechanical hardware in the fluid transfer system, to perform one or more actions relating to fluid transfer. For example, the user interface 1170 can receive and/or store (e.g., by user input or electronic transmission) the identity of the pharmacist or technician who is performing the fluid transfer, the identity of the patient, the name of the medical fluid, the volume of medical fluid to be transferred, the lot number, the expiration date of the medical fluid, and/or the date and time on which the fluid transfer was performed, etc. Also, as other examples, the user interface 1170 can assist in controlling the fluid transfer by receiving and conveying commands from the user via the user interface and/or displaying messages from the fluid transfer system regarding the progress and/or status of the fluid transfer, such as commands initiating the fluid transfer and/or halting the fluid transfer, and/or one or more messages demonstrating the amount of fluid transferred at any given moment, or the history of fluid transfers for a particular patient or pharmacist over a particular period, or one or more error messages indicating that the fluid transfer was not completed or that the fluid source container is not connected or is empty, or the fluid destination container is not connected or is full, or any other useful message.

As shown in FIG. 11, in some embodiments, the user interface 1170 can be universally compatible with a plurality of different fluid transfer devices 30 and a plurality of different types of fluid transfer devices 30, such as a fluid transfer device 1110, 1120, 1130, 1140 or 1150, etc. For example, a single user interface 1170 can be configured to electronically communicate with (e.g., by transferring data to and/or from) a plurality of different fluid transfer devices of the same type, or a plurality of different fluid transfer devices of a different type, that are performing separate fluid transfer operations, such as filling destination containers with a plurality of different therapeutic fluids and/or for a plurality of different patients. The user interface 1170 can be configured to simultaneously or generally concurrently control and/or record information from any or a plurality or all of such operations. The user interface 1170 can comprise a plurality of different communication capabilities, including a plurality of different electronic communicators and/or a plurality of different communication protocols for use with any of such electronic communicators. The user interface 1170 can be updated electronically to enable it to communicate electronically using protocols that are not originally used or installed on the user interface, which can enable the user interface 1170 to become compatible with future or different types of fluid transfer devices without requiring replacement of the fundamental components of the electronic communication system.

FIG. 12 is a front view of a medical device with a display and user interface, where the medical device is displaying downloaded infusion settings for confirmation or modification.

The infusion system 150 (FIG. 3) may prompt the caregiver to start the infusion by pressing the start button. When the caregiver presses the start button, a confirmation screen with the infusion settings programmed is presented for confirmation. When the caregiver presses the button to confirm, the infusion system 150 will begin delivering fluid according to the programmed settings. The infusion system 150s may send a status message to the central server 112 indicating that the infusion system 150 was successfully auto-programmed, confirmed and started by the caregiver and is now delivering fluid. In certain embodiments, the central server 112 continues to receive logs and status messages wirelessly from the infusion system 150 periodically as the infusion progresses or when alarms occur.

The nurse or caregiver reviews the infusion system 150 settings on a display 1220 of a user interface 1210 of the infusion system 150, presses a start button, and then is prompted with a confirmation screen to confirms the settings again as shown in FIG. 12. The nurse presses "yes" at a confirmation screen to actually start the infusion.

The nurse can adjust or modify the program settings on the system 150, if desired. Then, as illustrated in FIG. 12, the nurse may confirm or cancel the settings by pressing an appropriate button on a keypad 1215 or touching a designated area of the display 1210 when the display is a touch screen. Upon confirmation, the system 150 may prompt the nurse with a second screen asking if they are ready to start the infusion. Upon receipt of an affirmative response from the nurse, the infusion system 150 runs the programmed infusion.

In some embodiments, blockchain data management can be provided on the electronic label or in the electronic medical records system, and/or digital signatures can be provided, at each stage of compounding, storage, delivery, dispensing, and/or disposal. In some embodiments, each step of the filling, compounding, transportation, storage, infusion, and/or disposal of the medical fluid and/or the medical fluid container is performed, tracked, recorded, and/or verified in such a way as to greatly increase the speed of the medical fluid infusion process and lower the labor time and costs as compared to a manual system and to provide resistance against human mistake or malfeasance. In some embodiments, each step of the filling, compounding, transportation, storage, infusion, and/or disposal of the medical fluid and/or the medical fluid container is performed, tracked, recorded, and/or verified without requiring separate human data input (other than placing the machine-readable electronic label in proximity to one or more readers on the compounder, storage device, infusion pump, and/or disposal device, for data transfer).

Figure 13:
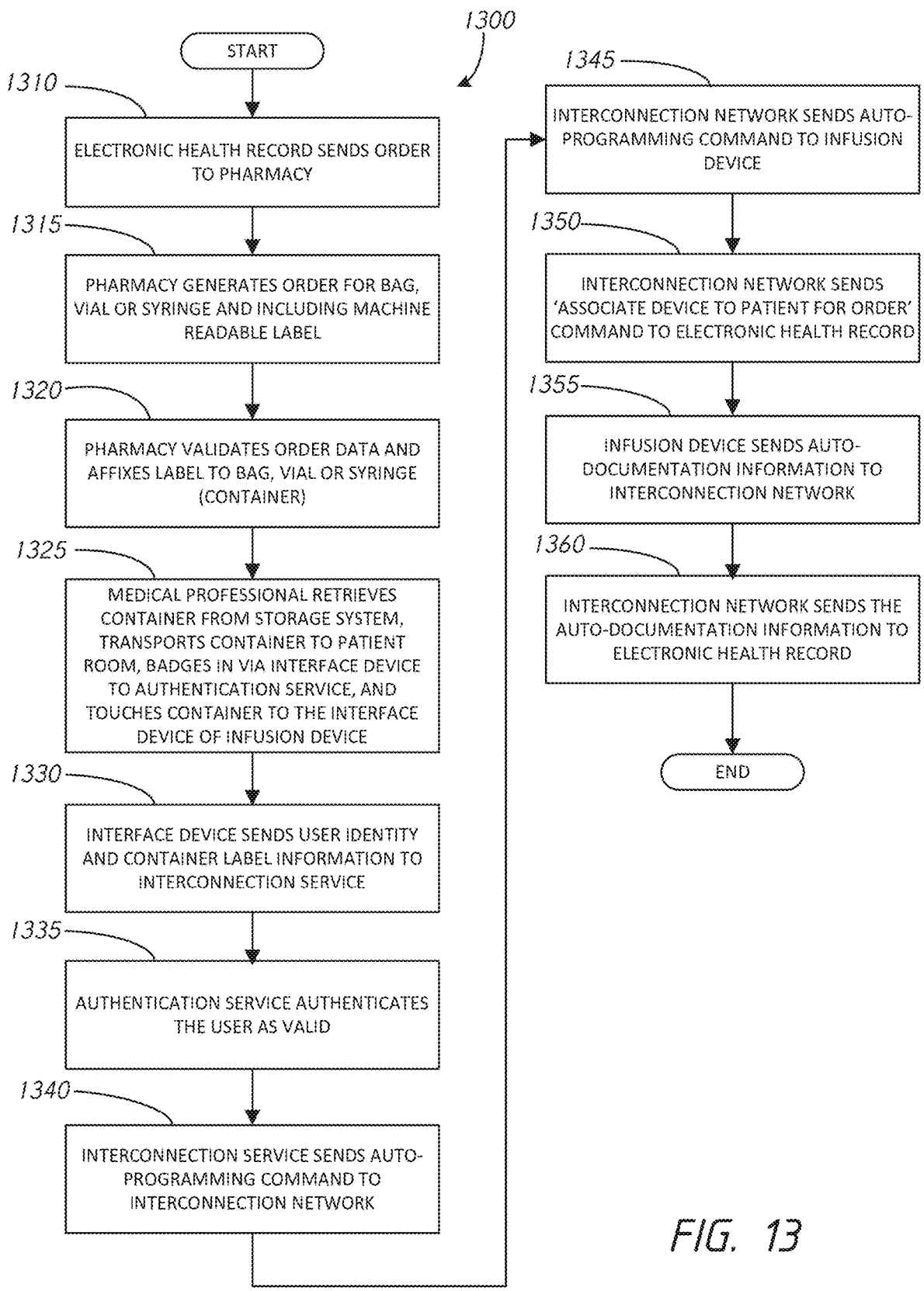
FIG. 13 is a flowchart of an example algorithm or process for intravenous infusion device programming utilizing an electronic machine readable label in a clinical setting such as may be performed using the example system shown in FIG. 1B.

FIG. 13 is a flowchart of an example algorithm or process 1300 for operation of the system in programming of an intravenous infusion device by utilizing machine readable electronic labels such as performed using the example system shown in FIG. 1B. In certain embodiments, the process 1300 may be performed by one or more of the processors associated with the pharmacy filling or compounding system 130, the infusion system 150 and the central server 112, examples of which are shown in FIGS. 1-3. In certain embodiments, the steps may be performed in a different order and/or certain steps may be combined and/or omitted. Beginning at a start step, process 1300 advances to a step 1310 where the electronic health record (EHR) sends a doctor's administration order to the pharmacy. Moving to a step 1315, the pharmacy generates the order for a fluids container (such as an IV bag, vial, or syringe), and prints a machine readable electronic label. Continuing at a step 1320, the pharmacy or other user validates the order data and affixes the label to the fluids container (e.g., bag, vial or syringe). Process 1300 advances to a step 1325 where a medical professional, e.g., nurse, retrieves the container from a storage system, takes it to a patient area or room, and presents machine-readable identification information to (e.g. "badges into") the system via an interface device, e.g., a dongle, puck or other interface circuit, to an authentication service.so as to verify the user's identity. The nurse then actuates the interface device (e.g. by touching or tapping the container with the affixed electronic label to the interface device) so that the information on the machine readable label is read. Continuing at a step 1330, the interface device sends the user identity and container label information to an interconnection service that is utilized in interconnecting the various devices of the system. Process 1300 continues at a step 1335 where the authentication service authenticates the user, e.g., nurse, as a valid user, such as via using a token. Advancing to a step 1340, the interconnection service sends an auto-programming (A/P) command to an interconnection network that connects to the various devices of the system. In certain embodiments, the interconnection network includes one or more processors and storages. Moving to a step 1345, the interconnection network sends the auto-programming command to an infusion device so as to provide instructions and/or data to the device for infusion of the container fluid. Proceeding to a step 1350, the interconnection network sends an "associate device to patient for order" command to the EHR such that the particular infusion device, the particular order and the particular patient are associated in the health record. Continuing at a step 1355, the infusion device sends auto-documentation (A/D) information to the interconnection network, and at step 1360, the interconnection network sends the A/D information to the EHR. Process 1300 then completes at an end state.

Figure 14:
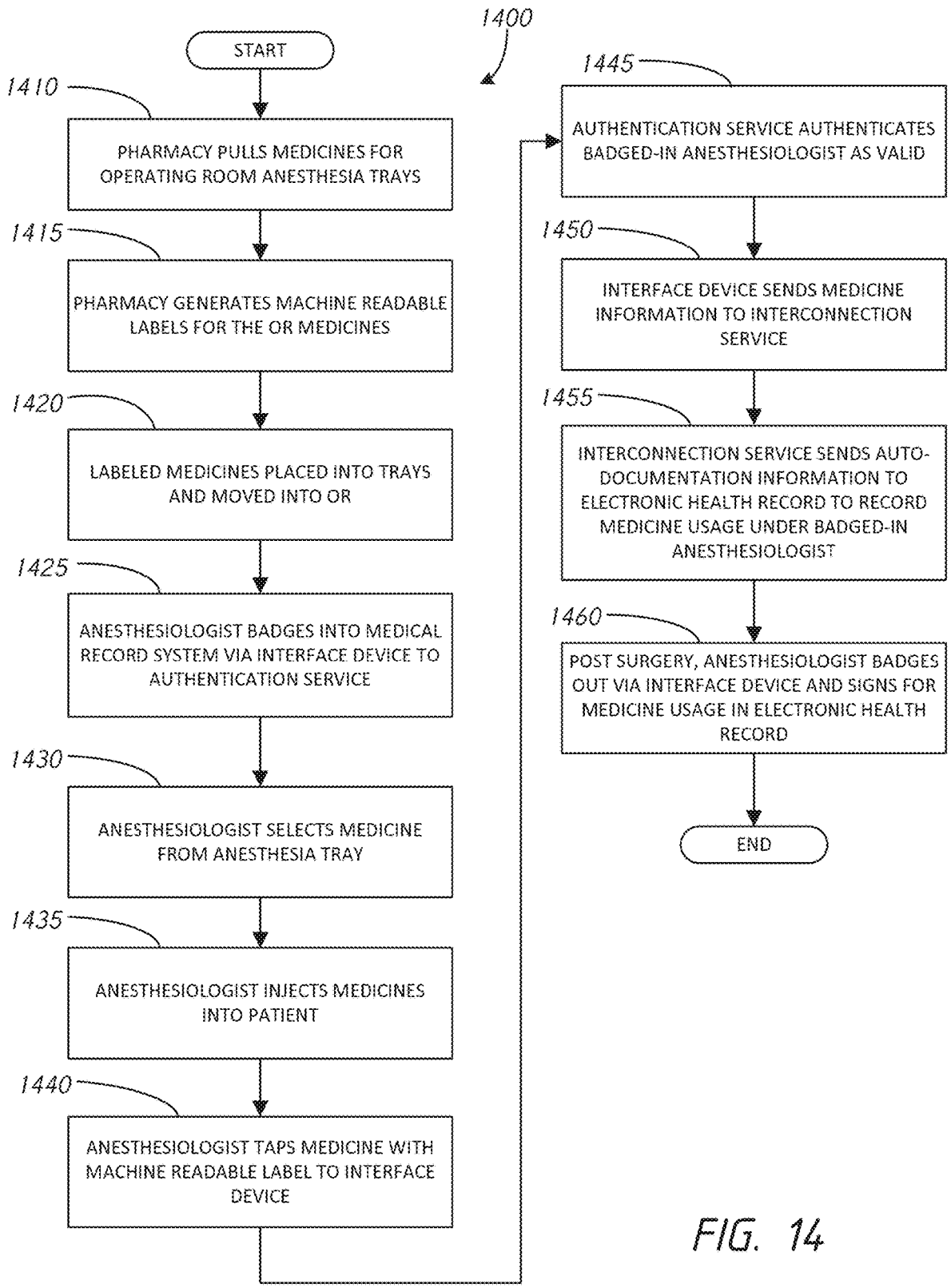
FIG. 14 is a flowchart of an example algorithm or process for intravenous label documentation in an operating room setting such as may be performed using a portion of the example system shown in FIG. 1B.

FIG. 14 is a flowchart of an example algorithm or process 1400 for operation of the system in documenting use of intravenous medicines in an operating room setting by utilizing machine readable electronic labels such as performed using portions of the example system shown in FIG. 1B. In certain embodiments, the process 1400 may be performed by one or more of the processors associated with the pharmacy filling or compounding system 130 and the central server 112, examples of which are shown in FIGS. 1-2. In certain embodiments, the steps may be performed in a different order and/or certain steps may be combined and/or omitted. Beginning at a start step, process 1400 advances to a step 1410 where a pharmacy associated with the operating room obtains medicines needed for an operating room medical procedure on a patient. Moving to a step 1415, the pharmacy generates and prints a machine readable electronic label for each medicine container. Continuing at a step 1420, the pharmacy affixes the electronic labels to each of the medicine containers and places them into one or more anesthesia trays, which are then moved into the operating room. Process 1400 advances to a step 1425 where pain-management professional, such as an anesthesiologist, presents electronically readable identifying information to the medical record system via an interface device, e.g., a dongle, puck or other interface circuit, to an authentication service.so as to verify the user's identity. Proceeding to a step 1430, the anesthesiologist picks up a medicine from the anesthesia tray, and injects the medicine into the patient at a step 1435. Advancing to a step 1440, the anesthesiologist then touches or taps the medicine container with the affixed electronic label to the interface device so that the information on the machine readable label is read. Continuing at a step 1445 of process 1400, the authentication service authenticates the user, e.g., anesthesiologist, as a valid user, such as via using a token. Proceeding to a step 1450, the interface device sends the medicine container label information to an interconnection service that is utilized in interconnecting the various devices of the system. Continuing at a step 1455, the interconnection service sends auto-documentation (A/D) information based on the label to the EHR so as to record medicine usage under the badged-in anesthesiologist. Advancing to a step 1460, after the surgery or other operating room procedure is completed, the anesthesiologist badges out via the interface device and signs for or confirms the medicine usage in the EHR. Process 1400 then completes at an end state.

Figure 15:
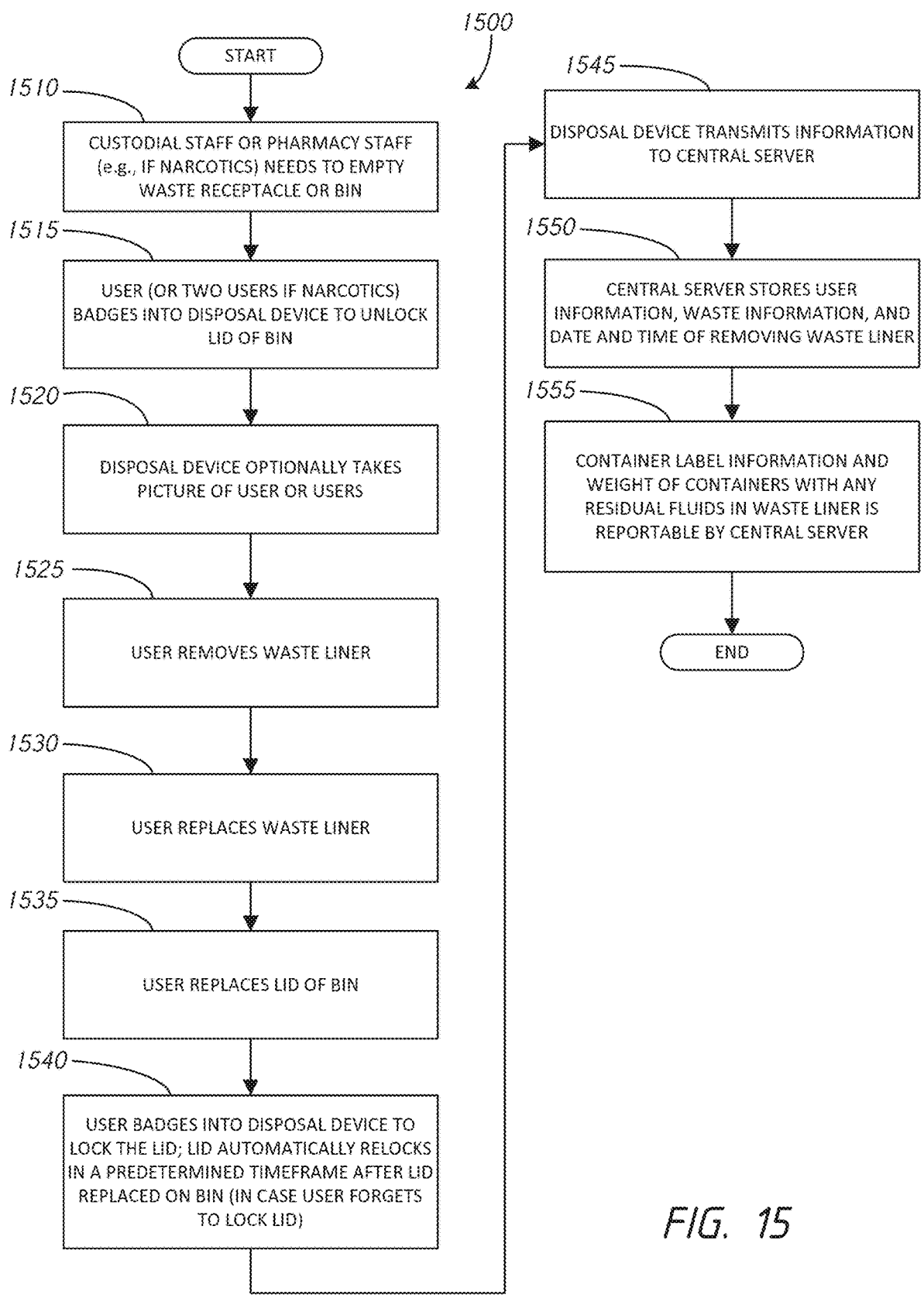
FIG. 15 is a flowchart of an example algorithm or process for cleaning of the disposal system such as may be performed using the example system shown in FIGS. 1B and 4.

FIG. 15 is a flowchart of an example algorithm or process 1500 for cleaning of the disposal system such as may be performed using the example systems shown in FIGS. 1B and 4. In certain embodiments, the disposal system may include multiple waste receptacles or bins, where each receptacle or bin has a lid that is lockable on the receptacle or bin. In normal operation of the disposable system, each lid is locked on its respective bin until a cleaning operation needs to be performed, which can be done at a certain capacity of a bin or at the end of each day or other time, for example. In certain embodiments, the steps may be performed in a different order and/or certain steps may be combined and/or omitted.

Beginning at a start step, process 1500 advances to a step 1510 where a custodial staff member or pharmacy staff member needs to empty one or more waste receptacles or bins. In certain embodiments, such as when the bin may contain narcotics, one or more pharmacy staff members, or hospital compliance or security personnel or others, may be required to perform the cleaning rather than a custodial staff member. Moving to a step 1515, one or more users presents identifying information at or near the disposal device, such as using the reader/interrogator 440 or other interface device, to unlock the lid on the bin. In certain embodiments, the disposal device uses the camera 444 to take a picture of each user at a step 1520.

Continuing at a step 1525 of process 1500, the user removes a waste liner having used medical containers therein from the unlocked bin for further disposal. Proceeding to a step 1530, the user replaces the waste liner with a new liner for the bin. Continuing at a step 1535, the user replaces lid on the newly lined bin. Moving to a step 1540, the user presents electronically readable identifying information at or near the disposal device to lock the lid on the bin. The lid automatically relocks within a predetermined number of seconds, for example, after being replaced on the bin (in case the user forgets to lock lid). Advancing to a step 1545 of process 1500, the disposal device transmits information to the central server, such as the name(s) and/or other identifying information of the user(s), the date and time, label information, and waste information including which bin of the disposal system was cleaned. Proceeding to a step 1550, the central server stores the transmitted information received from the disposal system. At a step 1555, label information and waste information, such as the weight of containers, which may have residual fluid, in the liner is reportable by the central server. Process 1500 then completes at an end state.

Figure 16:
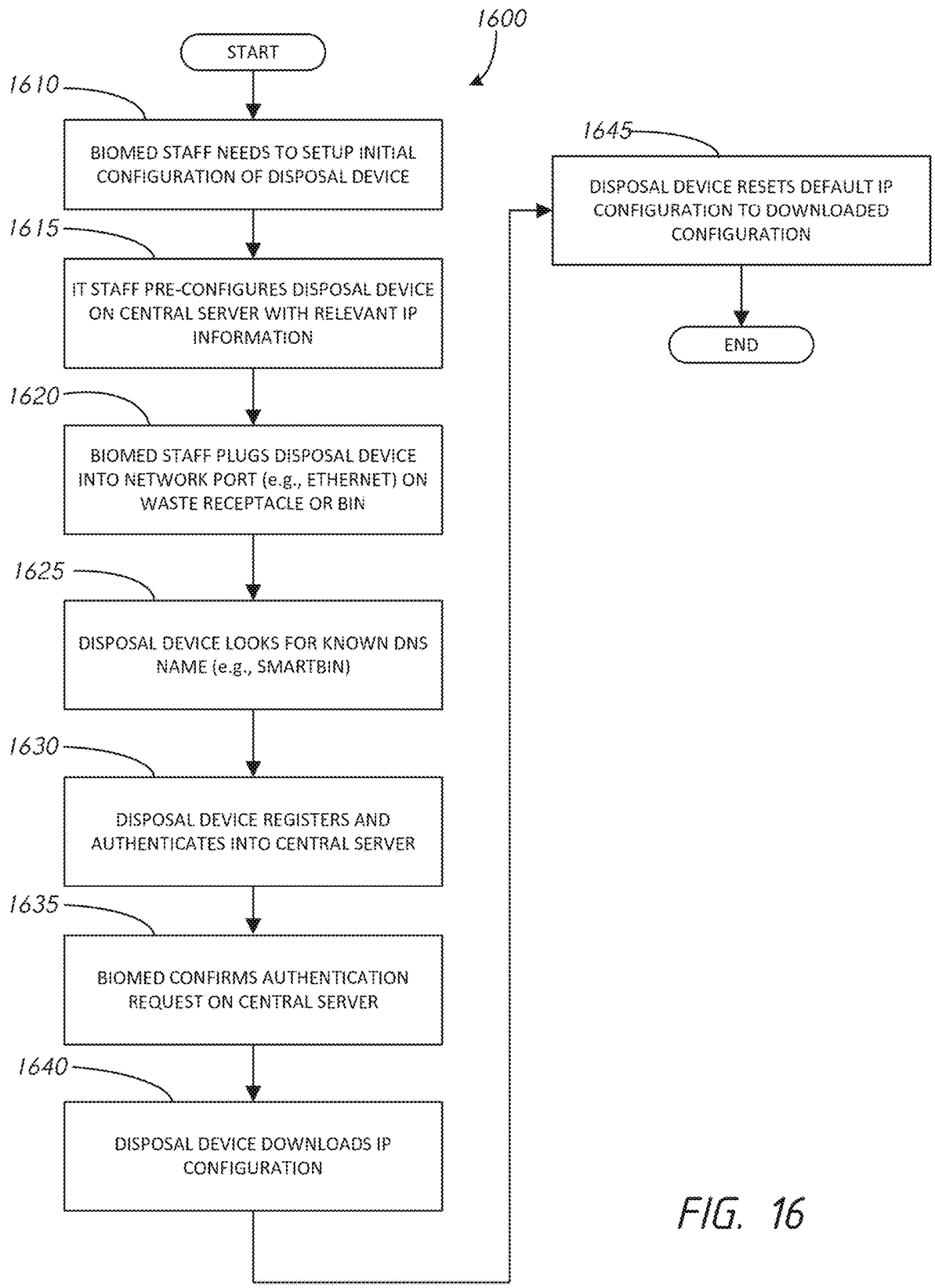
FIG. 16 is a flowchart of an example algorithm or process for initial configuration of the disposal system such as may be performed using the example system shown in FIGS. 1B and 4.

FIG. 16 is a flowchart of an example algorithm or process 1600 for initial configuration of the disposal system such as may be performed using the example systems shown in FIGS. 1B and 4. In certain embodiments, the disposal system may include multiple waste receptacles or bins. In certain embodiments, the steps may be performed in a different order and/or certain steps may be combined and/or omitted.

Beginning at a start step, process 1600 advances to a step 1610 where biomedical (Biomed) staff determines a need to perform a setup of the initial configuration of the disposal system, although other personnel may make that determination. Proceeding to a step 1615, IT staff or one or more other users pre-configures the disposal device on the central server with relevant IP (internet protocol) information. Continuing at a step 1620, Biomed staff plugs the disposal device into an Ethernet or other type of network port on each of the bins of the disposal system. Advancing to a step 1625, the disposal device checks for a known domain name system (DNS) name (e.g., smartbin), and at a step 1630, the disposal device registers and authenticates into the central server. Proceeding to a step 1635 of process 1600, Biomed confirms the authentication request on the central server. At a step 1640, the disposal device downloads the IP configuration, and then at a step 1645, resets the default IP configuration to the downloaded configuration. Process 1600 then completes at an end state.

Figure 17:
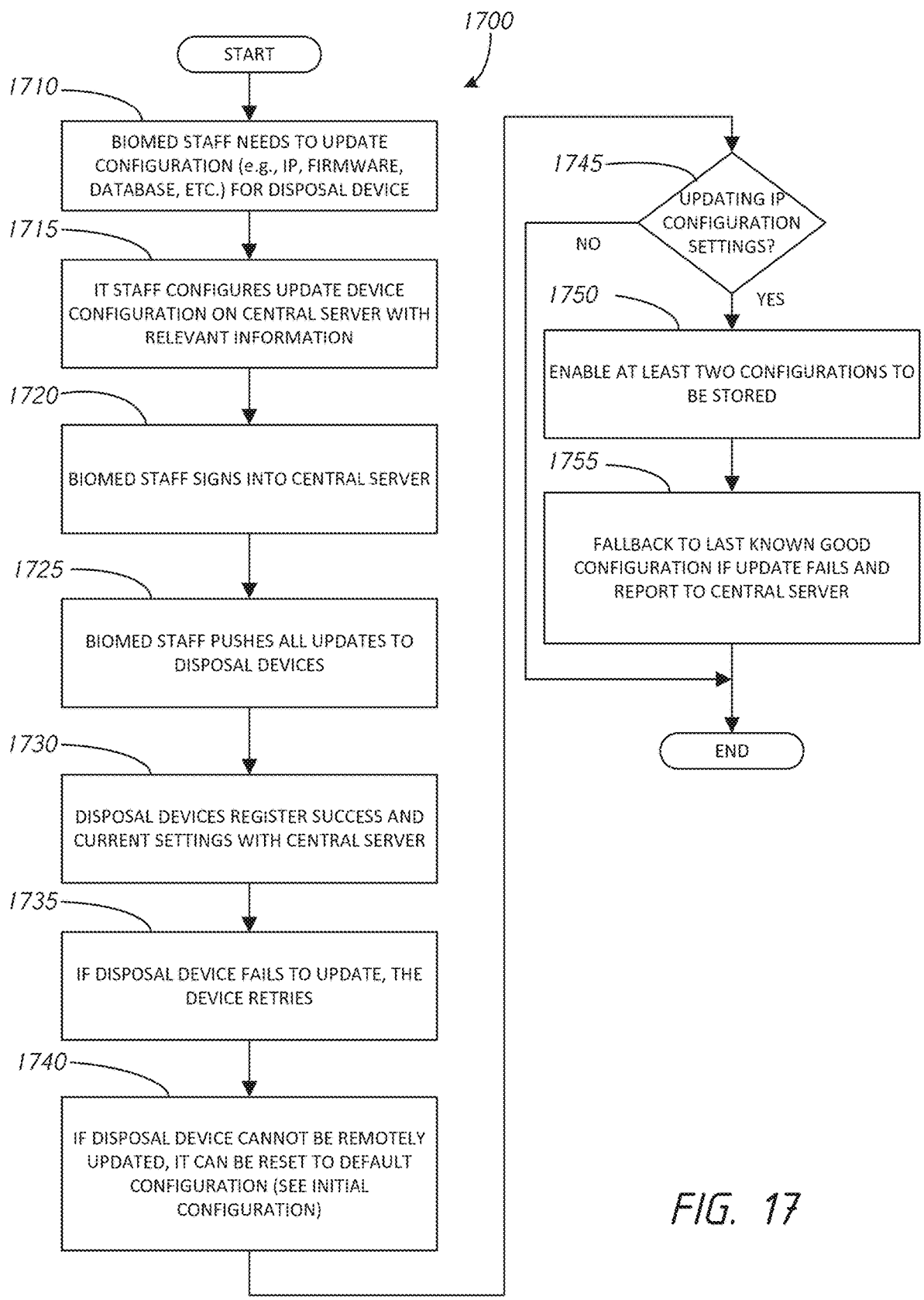
FIG. 17 is a flowchart of an example algorithm or process for updating a configuration of the disposal system such as may be performed using the example system shown in FIG. 1B.

FIG. 17 is a flowchart of an example algorithm or process 1700 for updating a configuration of the disposal system such as may be performed using the example system shown in FIG. 1B. In certain embodiments, the steps may be performed in a different order and/or certain steps may be combined and/or omitted.

Beginning at a start step, process 1700 advances to a step 1710 where biomedical (Biomed) staff determines a need to perform an update of the configuration (e.g., IP, firmware, database, etc.) of the disposal system, although other personnel may make that determination. Proceeding to a step 1715, IT staff configures an update device configuration for the disposal device on the central server with relevant information. Continuing at a step 1720, Biomed staff signs into the central server, and at a step 1725, pushes all updates to the disposal devices. Proceeding to a step 1730 of process 1700, the disposal devices register success and current settings with the central server. Continuing at a step 1735, if a disposal device fails to update, the device retries the update. Moving to a step 1740, in the event a device cannot be remotely updated, it can be reset to a default configuration (such as by following the steps on the initial configuration process above). Advancing to a decision state 1745, a determination is made if there is an update of the IP configuration settings (e.g., SSID, SSL, static IP, DHCP, DNS, etc.). If so, process 1700 continues at a step 1750 to enable at least two configurations to be stored. Proceeding to a step 1755, a fallback is enabled to the last known good configuration if the update fails and a report is made to the central server. However, if the decision state 1745 determines there is no update of the IP configuration settings, or at the completion of step 1755, process 1700 then completes at an end state.

Any of the systems, methods, and processes described in this specification can be used in situations in addition to or instead of the handling of opioids/narcotics. In some embodiments, weight measurement of the drug and reporting applies to other types of infusates. For example, in emergency room (ER) or operating room (OR) settings, there are fast-paced environments where the recording of drugs used is secondary to the preservation of life. In these situations, the disposal device may be associated with a patient. The information about the drugs that are disposed of in the disposal device can be sent to the EHR for confirmation that they should be recorded in the patient's chart and/or billed to the patient's account.

By way of confirmation, any medication or therapeutic material or drug in any form or container, including pills, liquids, powders, topicals, injectables such as syringes, etc., can be electronically labeled/tagged, such as by use of RFID, either when prepared on site by the pharmacy or other user, or when pre-filled or pre-packaged, or in any other stage, and/or recorded into the EHR, or otherwise processed or handled or disposed of in accordance with any of the steps or using any of the components, systems, or subsystems described and/or illustrated in this specification.

Although this invention has been disclosed in the context of certain embodiments and examples, it will be understood by those skilled in the art that the present invention extends beyond the specifically disclosed embodiments to other alternative embodiments and/or uses of the invention and equivalents thereof. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the disclosed invention. Thus, it is intended that the scope of the present invention herein disclosed should not be limited by the particular disclosed embodiments described above, but should be determined only by a fair reading of the claims that follow.

The following is claimed:

1. A medical system for providing intravenous fluid to a patient, the
medical system comprising:
a medical intravenous fluid filling system comprising a motor configured to transfer liquid from a liquid source container to a liquid destination container, the filling system configured to: (a) receive an electronic medication order at the filling system; (b) record information onto an electronic communication device, the information including drug information, patient information, and intravenous administration information, the electronic communication device being attached to the liquid destination container; and (c) transfer liquid from the liquid source container to the liquid destination container using the medical intravenous fluid filling system so that the liquid destination container contains a liquid with a drug identified by the drug information;
an intravenous infusion pump capable of: (a) receiving the recorded information through an electronic reader integrated into the infusion pump, including drug information, patient information, and intravenous administration information, from the electronic communication device on the liquid destination container; (b) automatically programming an infusion course into the intravenous infusion pump in response to the received recorded information without requiring a user to manually input any of the information regarding the fluid to be infused, the manner of administration of the fluid, or the patient into the intravenous infusion pump; and (c) writing information to the electronic communication device through an electronic writer to note a change in contents of the liquid destination container;
wherein automatically programming the infusion course into the intravenous infusion pump includes automatically populating a screen of the intravenous infusion pump with the received information from the electronic communication device on the liquid destination container for the infusion course; and
a disposal device capable of receiving one or more portions of the recorded information automatically from the electronic communication device on the liquid destination container after patient infusion, the recorded information including a changed portion of the recorded information indicating the change in contents of the liquid destination container, the disposal device being capable of receiving and securing the liquid destination container with the any remaining liquid contained therein into the disposal device such that the liquid destination container is beyond the reach of or access by the user; and after the liquid destination container with the any remaining liquid contained therein is positioned inside of the disposal device, evaluating the any remaining liquid within the liquid destination container to determine one or more physical, optical, or chemical characteristics of the liquid within the liquid destination container, and comparing the one or more physical, optical, or chemical characteristics to the changed portion of the recorded information received from the electronic communication device on the liquid destination container.

2. The medical system of claim 1, wherein the disposable device is capable of capturing and recording a person's identity.

3. The medical system of claim 1, wherein the system is configured to match a patient's information with one or more infusion devices known to be assigned to the patient to resist mistaken infusion of a drug.

4. The medical system of claim 1, wherein the intravenous infusion pump is configured to automatically determine a volume or weight of infused drug and electronically record the infused volume or weight on the electronic communication device attached on the liquid destination container.

5. A system for providing an intravenous medication, the system comprising:

a medical liquid container with an electronic communication device;
a medical liquid filling system configured to record information onto the electronic communication device, the information including drug information for identifying a drug to be contained within the liquid container, patient information, and intravenous administration information;
a reader configured to read the recorded information on the electronic communication device on the liquid container;
a patient intravenous infusion pump configured to communicate with the reader, wherein an infusion course can be automatically programmed into the intravenous infusion pump using the recorded information without requiring a user to manually input any of the drug information, patient information, or intravenous administration information, wherein automatically programming the infusion course into the intravenous infusion pump includes automatically populating a screen of the intravenous infusion pump with the read information from the electronic communication device on the liquid container for the infusion course;
a writer configured to write information to the electronic communication device to update or modify the contents of the medical liquid container; and
a secure disposal device configured to: (1) receive the liquid container with any remaining liquid contained therein after use in a manner that places the liquid container beyond access by a user; (2) within the disposal device, evaluate the any remaining liquid within the liquid container to determine one or more physical, optical, or chemical characteristics of the liquid within the liquid container; (3) receive one or more portions of the recorded information from the electronic communication device on the medical liquid container, including the information representing updated or modified contents; and (4) compare the one or more physical, optical, or chemical characteristics to the information representing the updated or modified contents of the recorded information received from the electronic communication device of the medical liquid container.

6. The system of claim 5, wherein the disposal device is configured to confirm chemical contents of the liquid container.

7. The system of claim 6, wherein the disposal device is configured to generate spectrographic identification of the contents of the liquid container.

8. The system of claim 6, wherein the disposal device is configured to capture an identity and a picture of a person operating the disposal device.

9. The system of claim 8, wherein the disposal device is configured to capture an electronic image of the person operating the disposal device.

10. The system of claim 5, wherein the system is configured to generate an alert when an original weight of the drug in the transferred liquid container is not equal to an infused weight of the drug plus the weight of the remaining liquid.

11. The system of claim 5, additionally comprising a reader in communication with the disposal device, the reader configured to automatically read the information from the electronic communication device on the liquid container transferred after patient infusion.

12. The system of claim 5, wherein the disposal device is configured to weigh any residual drug of the transferred liquid container.

13. The system of claim 5, wherein the disposal device is configured to capture an electronic image of the transferred liquid container.

14. A method of using the system of claim 5, wherein automatically programming an infusion course into the intravenous infusion pump in response to the received information from the electronic communication device is performed at a patient location.

15. A method of using the system of claim 1, wherein automatically programming an infusion course into the intravenous infusion pump in response to the received recorded information is performed without requiring the intravenous infusion pump to calculate portions of the infusion course or without requiring data generated from sensors.

16. A method of using the system of claim 5, wherein automatically programming an infusion course into the intravenous infusion pump in response to the received recorded information is performed without requiring the intravenous infusion pump to calculate portions of the infusion course or without requiring data generated from sensors.

17. A method of using the system of claim 5, comprising the step of permitting the user to confirm infusion settings.

18. A method of using the system of claim 5 comprising capturing an image of a person who is positioning the liquid destination container in the disposal device.

19. The system of claim 5, wherein the reader is part of the intravenous infusion pump.

20. The system of claim 5, wherein the filling system is configured to transfer medical liquid from medical vials to medical IV bags.

* * * * *